United States Patent
Galland et al.

(10) Patent No.: US 7,253,298 B2
(45) Date of Patent: Aug. 7, 2007

(54) PROCESS FOR PREPARING NITRILE COMPOUNDS FROM ETHYLENICALLY UNSATURATED COMPOUNDS

(75) Inventors: Jean-Christophe Galland, Lyons (FR); Blaise Didillon, Francheville (FR); Philippe Marion, Vernaison (FR); Damien Bourgeois, Lyons (FR)

(73) Assignee: Rhodia Polyamide Intermediates, Saint-Fons (FR)

( * ) Notice: Subject to any disclaimer, the term of this patent is extended or adjusted under 35 U.S.C. 154(b) by 0 days.

(21) Appl. No.: 11/166,595

(22) Filed: Jun. 24, 2005

(65) Prior Publication Data

US 2006/0100455 A1    May 11, 2006

Related U.S. Application Data

(63) Continuation of application No. 10/521,324, filed as application No. PCT/FR03/02191 on Jul. 11, 2003.

(51) Int. Cl.
*C07C 253/10* (2006.01)
*C07F 9/02* (2006.01)

(52) U.S. Cl. .................. 558/332; 558/156; 558/162; 546/22; 549/220; 549/221

(58) Field of Classification Search ................ 558/332, 558/156, 162; 546/22; 549/220, 221
See application file for complete search history.

(56) References Cited

U.S. PATENT DOCUMENTS

| 5,360,938 A | 11/1994 | Babin et al. ................. 568/449 |
| 5,512,696 A | 4/1996 | Kreustzer et al. ........... 558/338 |
| 6,020,516 A | 2/2000 | Foo et al. .................... 558/338 |
| 6,069,267 A | 5/2000 | Tam ............................ 558/95 |

FOREIGN PATENT DOCUMENTS

| EP | 0518541 | 12/1992 |
| WO | WO01014392 | 1/2001 |

OTHER PUBLICATIONS

CA No. 70:68955.
CA No. 68:115380.
CA No. 65:91373.
CA No. 61:3507.
CA No. 60:67371.
International Search Report of WO 2004/007435.

*Primary Examiner*—Rebecca Anderson
*Assistant Examiner*—Yong Chu

(57) ABSTRACT

The present invention concerns a process for hydrocyanating ethylenically unsaturated organic compounds to compounds containing at least one nitrile function. It relates more particularly to the hydrocyanation of diolefins such as butadiene or of substituted olefins such as alkenenitriles, for instance pentenenitriles. According to the process of the invention the reaction is implemented in the presence of a metal complex catalyst comprising a transition metal such as nickel and an organic ligand.

17 Claims, No Drawings

PROCESS FOR PREPARING NITRILE COMPOUNDS FROM ETHYLENICALLY UNSATURATED COMPOUNDS

This application is a continuation of U.S. application Ser. No. 10/521,324, filed on Sep. 14, 2005, which is an application under 35 U.S.C. Section 371 of International Application Number PCT/FR2003/002191 filed on Jul. 11, 2003.

The present invention concerns a process for hydrocyanating ethylenically unsaturated organic compounds to compounds containing at least one nitrile function.

It relates more particularly to the hydrocyanation of diolefins such as butadiene or of substituted olefins such as alkenenitriles, for instance pentenenitriles. The hydrocyanation of butadiene to pentenenitriles is an important reaction which has been implemented industrially for a number of years, particularly in the process for synthesizing adiponitrile, a major chemical intermediate which allows access in particular to the monomers of numerous polymers, foremost among which are the polyamides.

French patent 1 599 761 describes a process for preparing nitrites by addition of hydrocyanic acid with organic compounds having at least one ethylenic double bond, in the presence of a nickel catalyst and a triaryl phosphite. This reaction may be conducted in the presence or absence of a solvent.

When a solvent is used in this prior art process it is preferably a hydrocarbon, such as benzene or xylenes, or a nitrile such as acetonitrile.

The catalyst employed is an organometallic complex of nickel, containing ligands such as phosphines, arsines, stibines, antimonites, arsenites, phosphites, phosphinites or phosphonites.

The processes for hydrocyanating dienes generally comprise two steps: a first hydrocyanation, leading to branched and linear unsaturated mononitriles, and a second step which allows the dinitriles to be obtained.

Often only the linear nitrites are of interest for the synthesis of new products such as, for example, adiponitrile. These processes therefore also include an intermediate step, which is referred to as the isomerization step and consists in treating the branched unsaturated mononitriles to convert them into linear unsaturated mononitriles.

The presence of a promoter to activate the catalyst, such as a boron compound or a metal salt, generally a Lewis acid, is also recommended for carrying out the second step.

Patent FR-A-2 338 253 proposed carrying out the hydrocyanation of compounds having at least one ethylenic unsaturation in the presence of an aqueous solution of a compound of a transition metal, particularly nickel, palladium or iron, and of a sulphonated phosphine.

The sulphonated phosphines described in said patent are sulphonated triarylphosphines and more particularly sulphonated triphenylphosphines.

This process permits proper hydrocyanation, particularly of the butadiene and the pentenenitriles, easy separation of the catalytic solution, by simple decanting, and, consequently, goes as far as possible to avoid the discharge of effluent or of waste containing the metals used as catalyst.

Research has nevertheless been conducted in order to find new catalytic systems which give greater performance in terms of catalytic activity and of selectivity and stability.

One of the aims of the present invention is to propose a new class of ligands which with the transition metals make it possible to obtain catalytic systems exhibiting in particular an improved selectivity to linear nitriles as compared with the known systems.

The present invention accordingly provides a process for hydrocyanating a hydrocarbon compound containing at least one ethylenic unsaturation by reacting it in a liquid medium with hydrogen cyanide in the presence of a catalyst comprising a metallic element selected from transition metals and an organic ligand, characterized in that the organic ligand corresponds to the general formula I below:

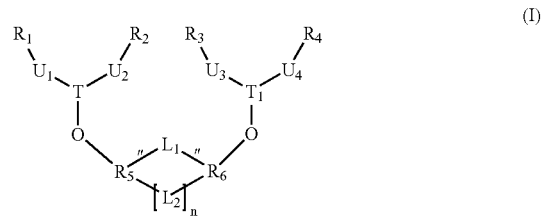

in which:

T and $T_1$, which are identical or different, represent a phosphorus, arsenic or antimony atom, $R_1$, $R_2$, $R_3$ and $R_4$, which are identical or different, represent a substituted or unsubstituted, aromatic, aliphatic or cycloaliphatic radical comprising one or more rings, which are in fused form or not and which may contain one or more heteroatoms, where the radicals $R_1$ and $R_2$ on the one hand and $R_3$ and $R_4$ on the other hand may be interconnected by a covalent bond, a hydrocarbon chain or a heteroatom, $U_1$, $U_2$, $U_3$ and $U_4$, which are identical or different, represent an oxygen atom or a radical of formula NR in which R denotes a monovalent alkyl, aryl, cycloalkyl, sulphonyl or carbonyl radical, $R_5$ and $R_6$, which are identical or different, represent an aryl or cycloaliphatic group which may comprise heteroatoms and/or one or more rings, in fused form or not, and which are substituted or unsubstituted, n is an integer equal to 0 or 1, $L_1$, when n is 0, represents a divalent radical selected from the group consisting of the groups $NR_7$, $PR_8$, $SiR_9R_{10}$, $BR_{11}$, S, $POR_{12}$, $SO_2$ and CO, in which $R_7$ is as defined for R above, $R_8$ and $R_{12}$ may represent the radical $OR_{13}$, and $R_8$, $R_9$, $R_{10}$, $R_{11}$, $R_{12}$ and $R_{13}$ represent alkyl, aryl or cycloalkyl radicals, $L_1$ and $L_2$, when n is 1, are identical or different and represent a covalent bond or a radical selected from the group consisting of the groups O, $NR_7$, $PR_8$, $SiR_9R_{10}$, $BR_{11}$, S, $POR_{12}$, $So_2$, CO and —$CR_{14}R_{15}$—, in which $R_7$ is as defined for R above, $R_8$ and $R_{12}$ may represent the radical $OR_{13}$, and $R_8$, $R_9$, $R_{10}$, $R_{11}$, $R_{12}$, $R_{13}$, $R_{14}$ and $R_{15}$ represent alkyl, aryl or cycloalkyl radicals, it being possible also for $R_{14}$ and $R_{15}$ to represent a hydrogen atom.

Examples of structures

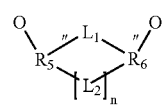

include the following formulae listed in Table I below:

TABLE I
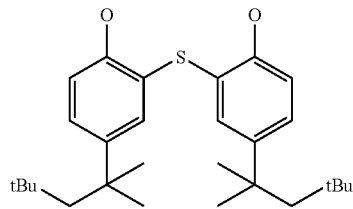
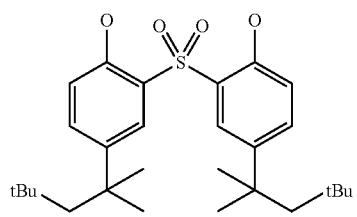
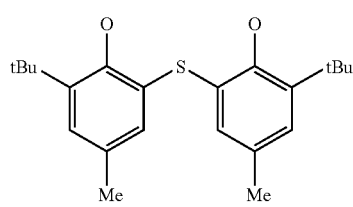
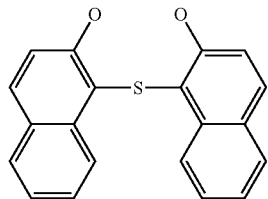
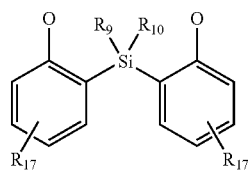
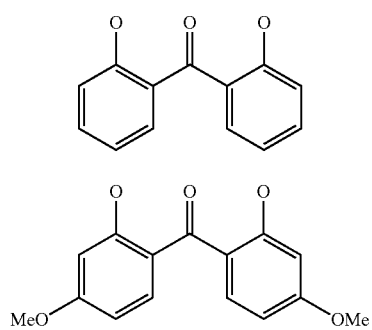
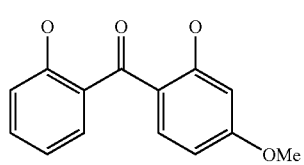
TABLE I-continued
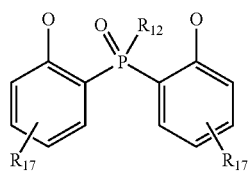
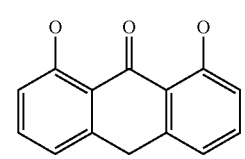
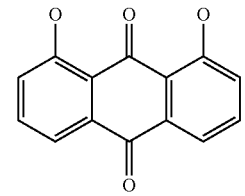
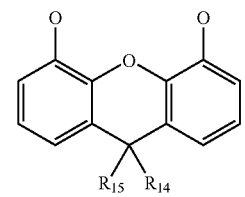
in which $R_{17}$ represents an alkyl, aryl, halogen, alkoxy, thiol, cyano, nitro, aryloxy, alkoxycarbonyl, acyl or formyl radical.
Ligands in accordance with the invention include the following compounds listed in Table II below:
TABLE II
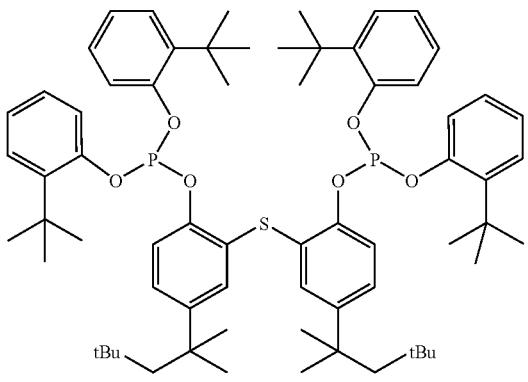

TABLE II-continued
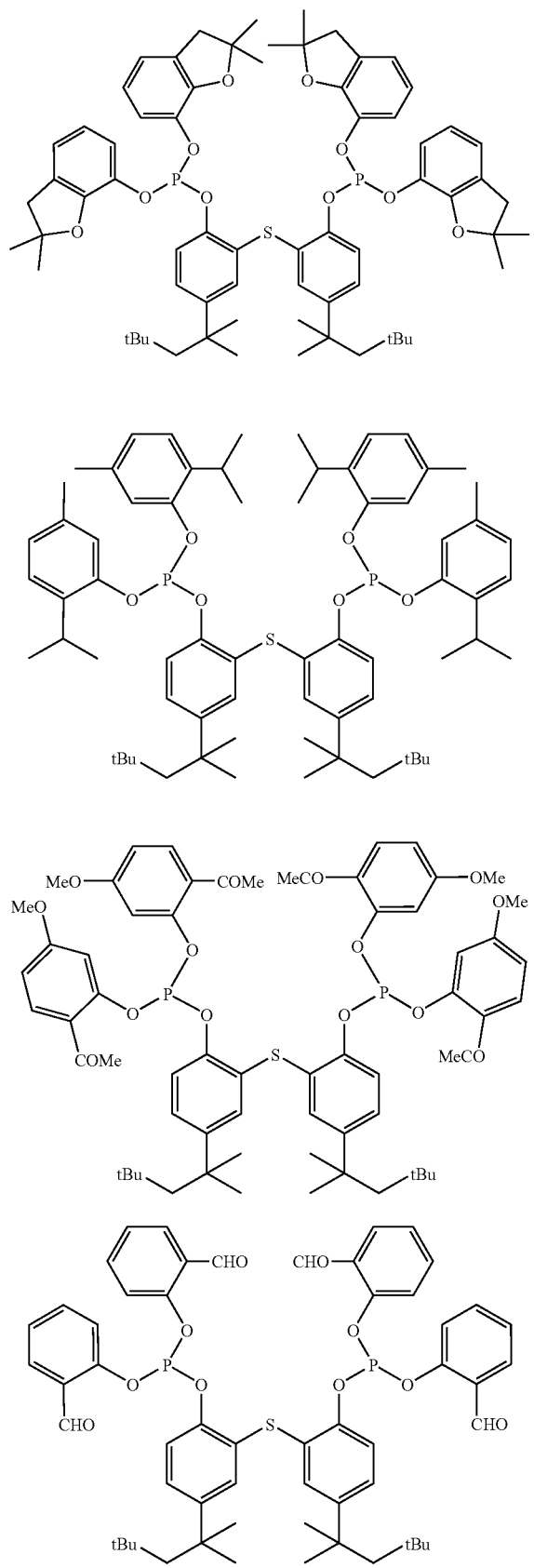
TABLE II-continued
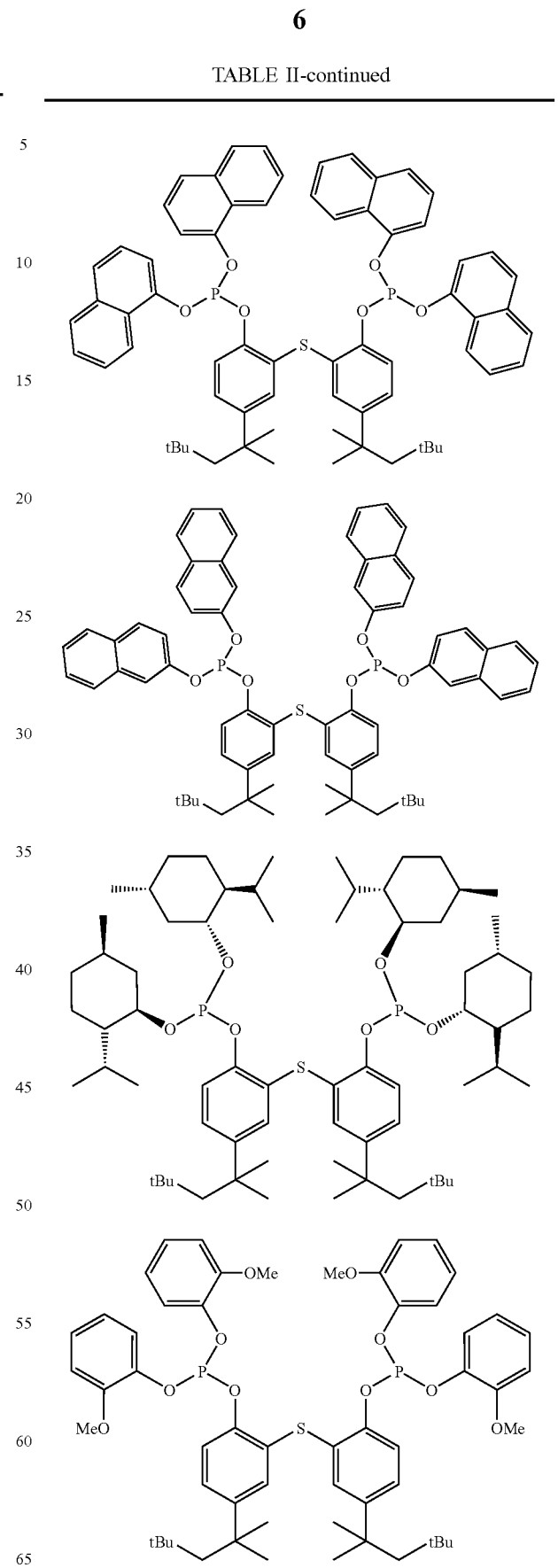

TABLE II-continued
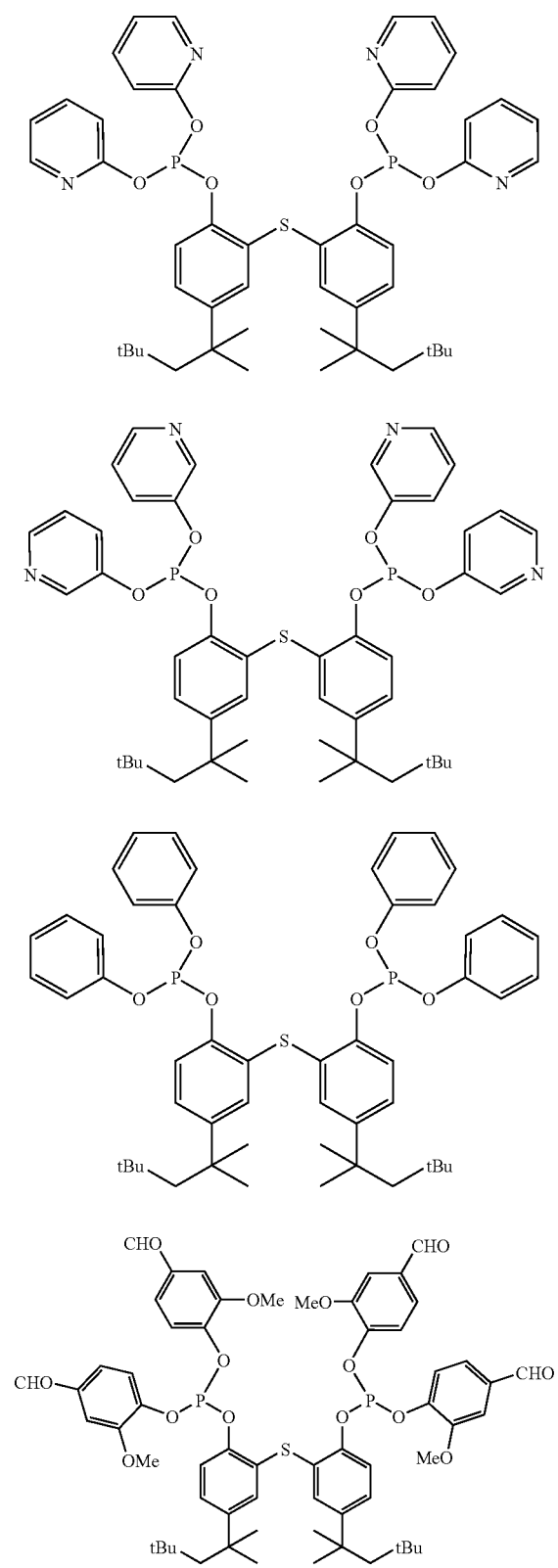
TABLE II-continued
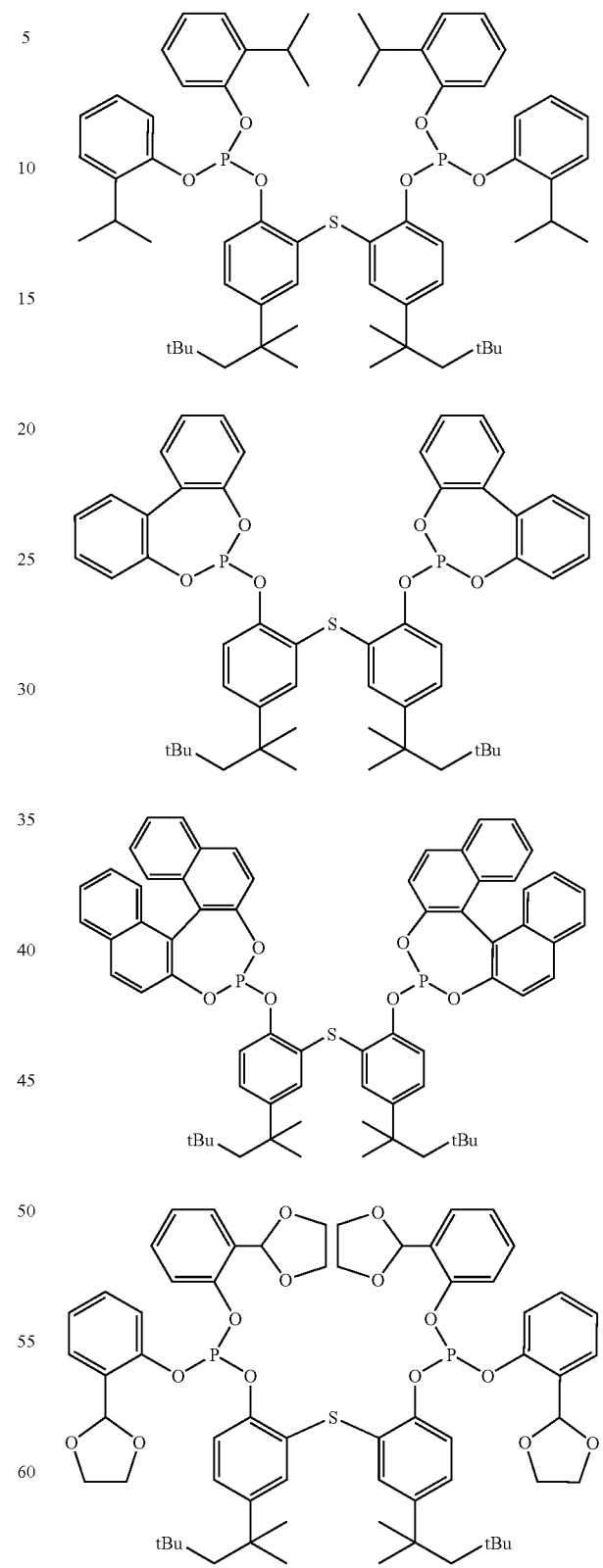

TABLE II-continued
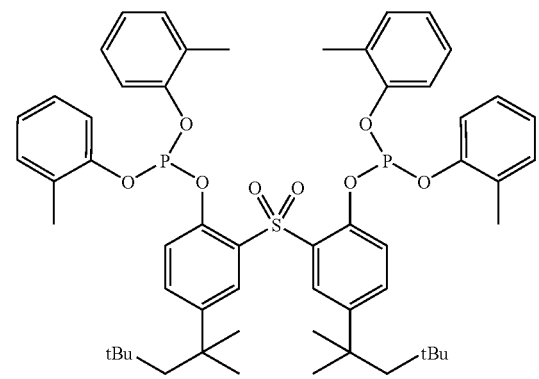
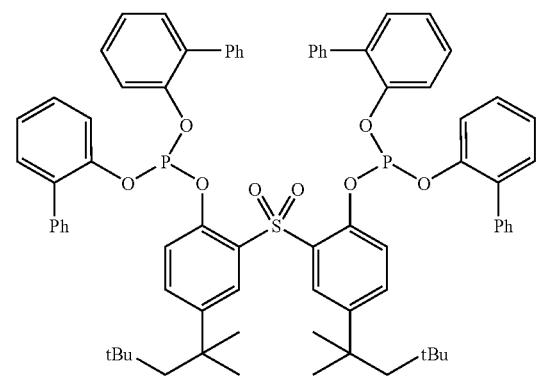
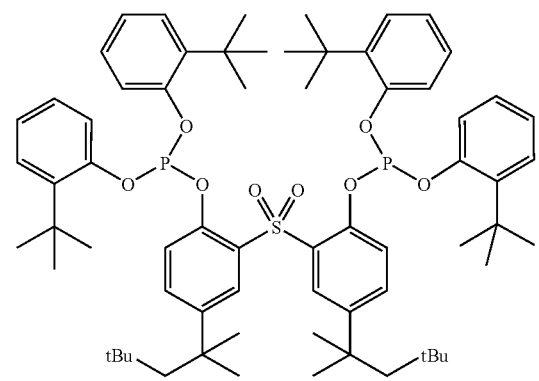
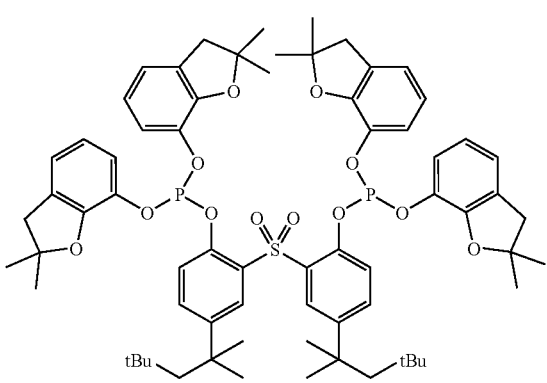
TABLE II-continued
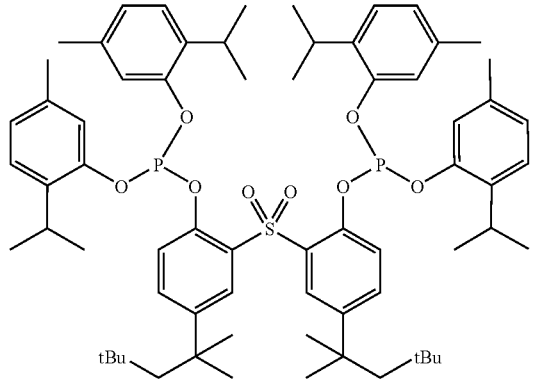
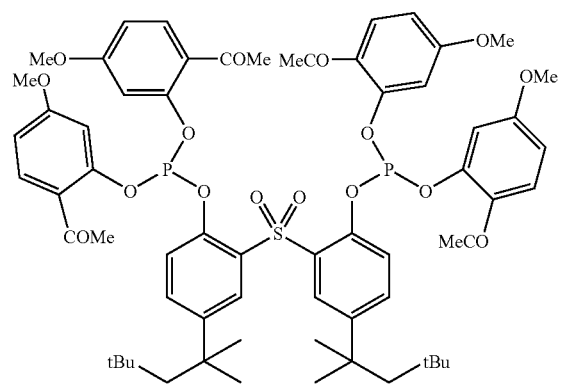
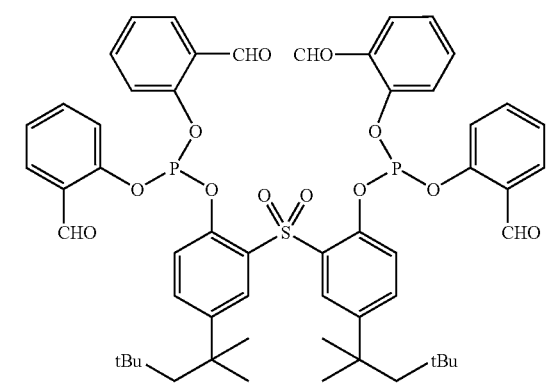
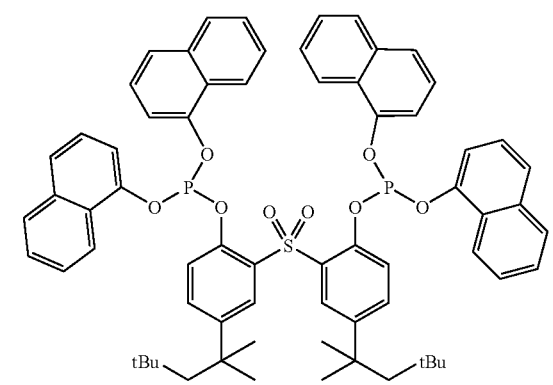

TABLE II-continued
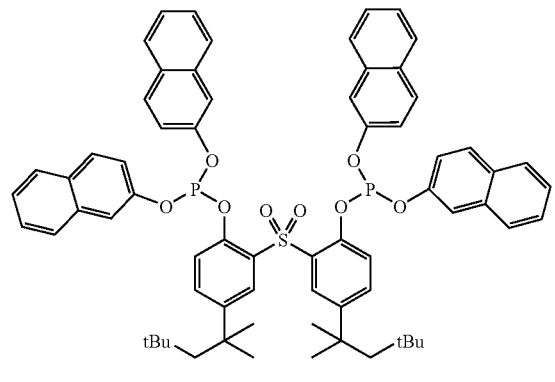
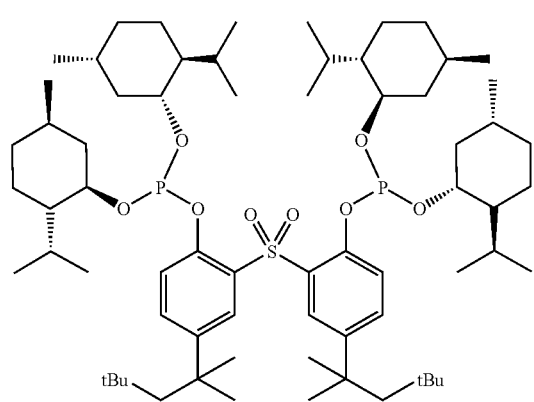
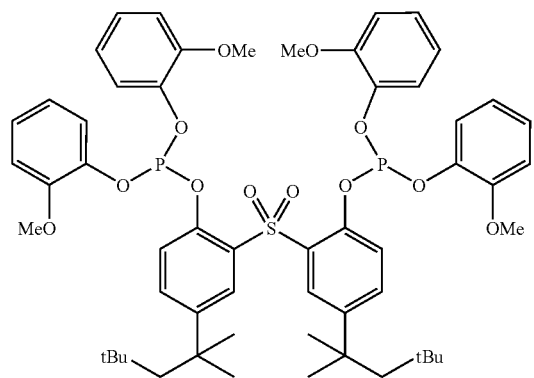
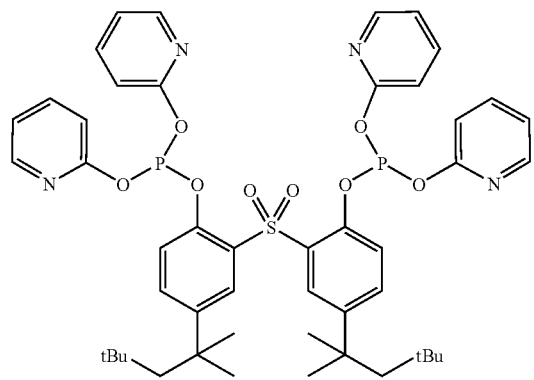
TABLE II-continued
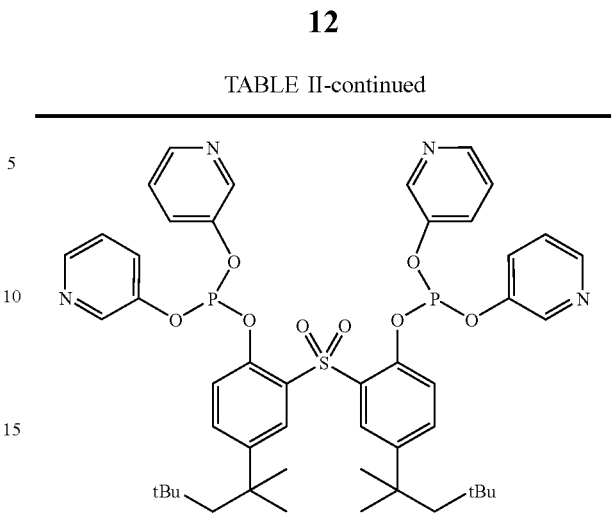
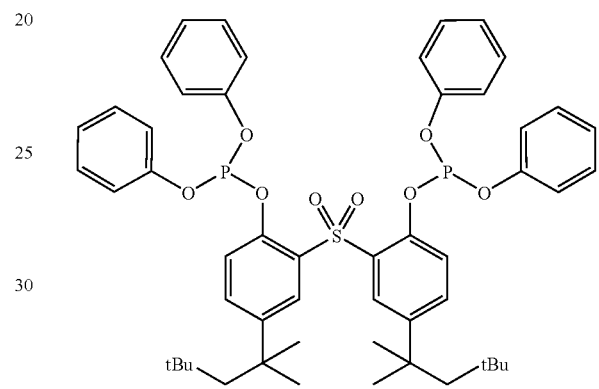
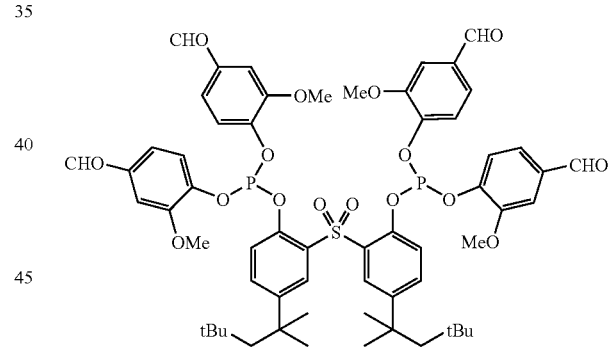
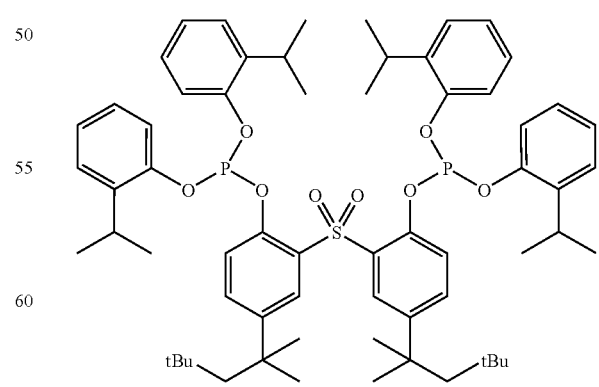

TABLE II-continued
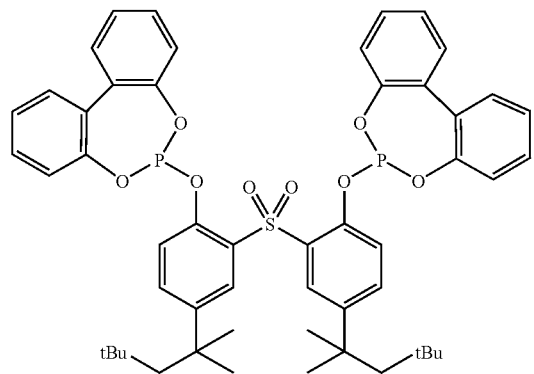
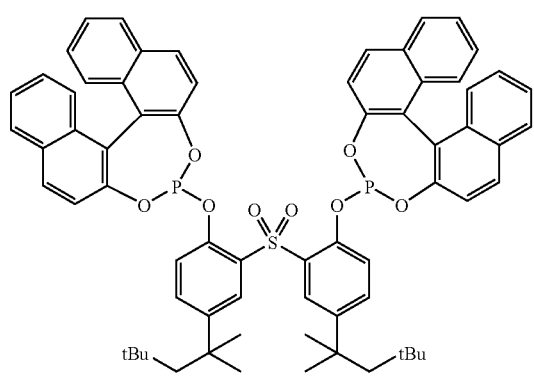
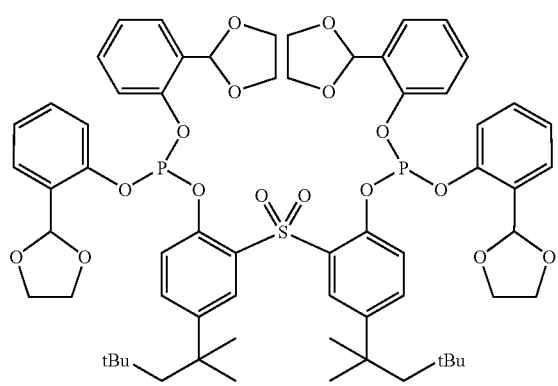
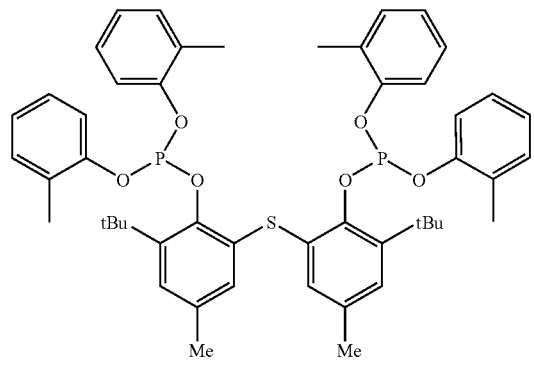
TABLE II-continued
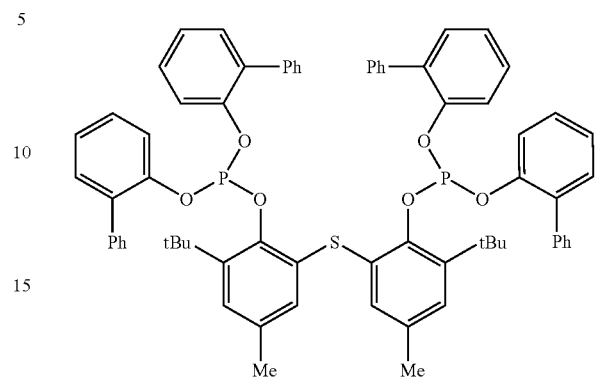
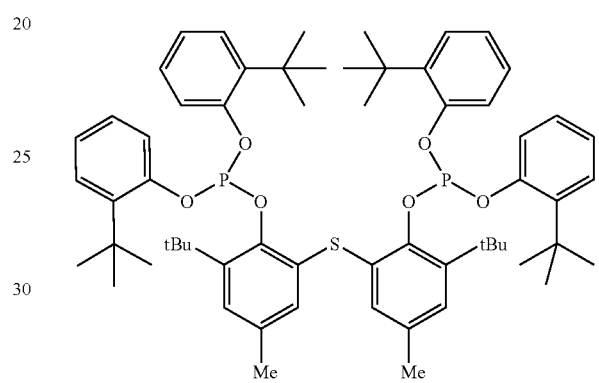
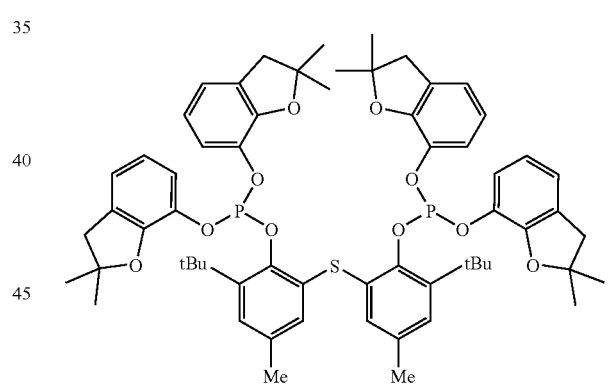
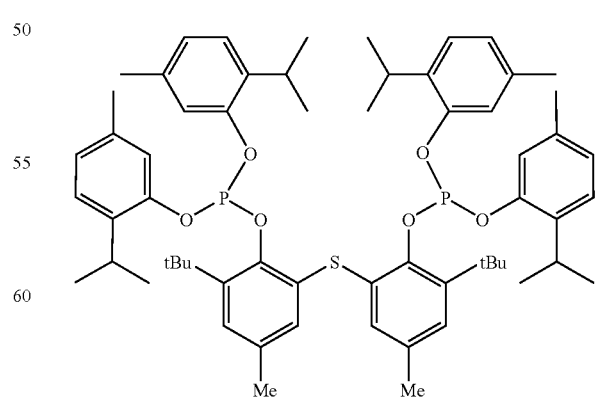

TABLE II-continued
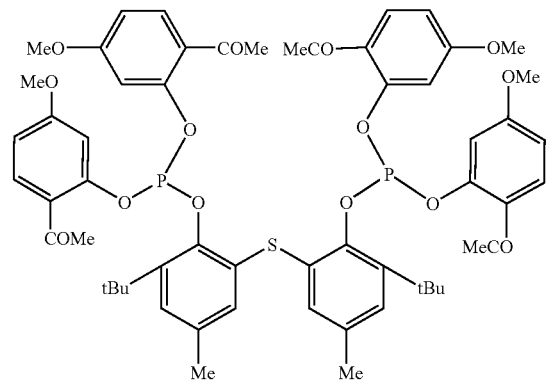
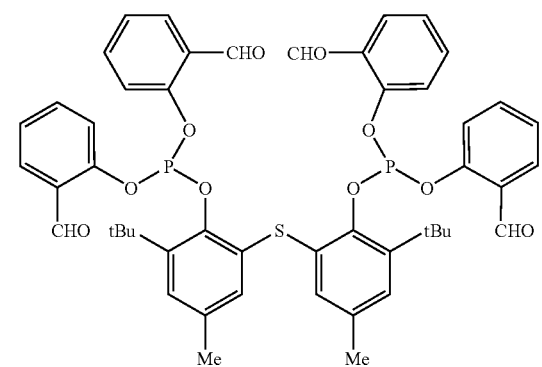
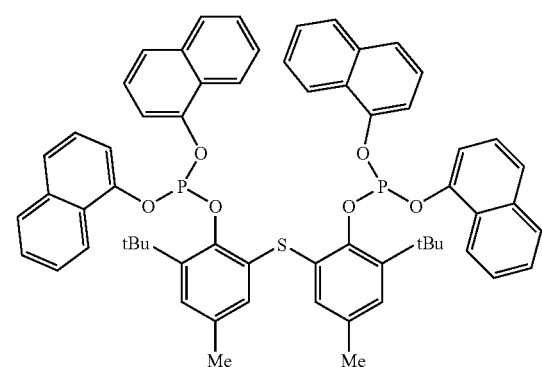
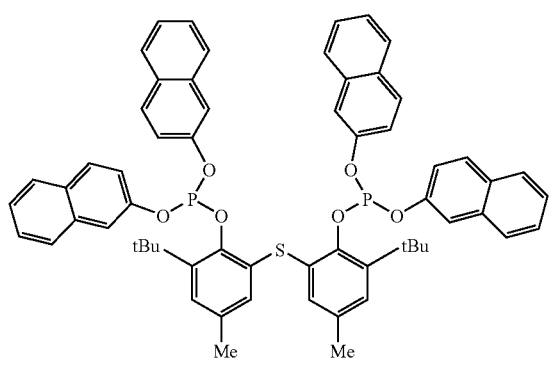
TABLE II-continued
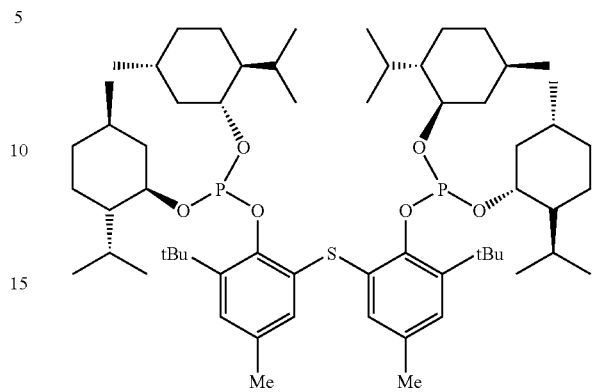
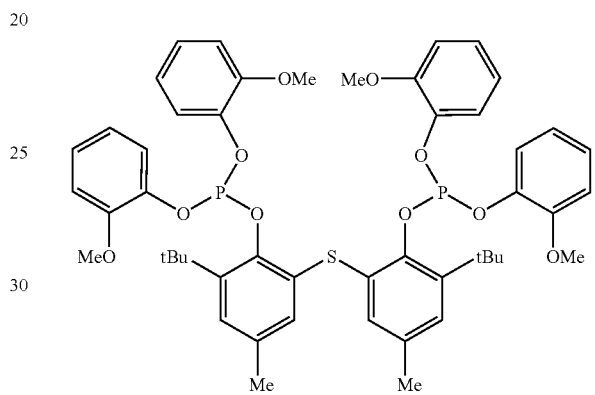
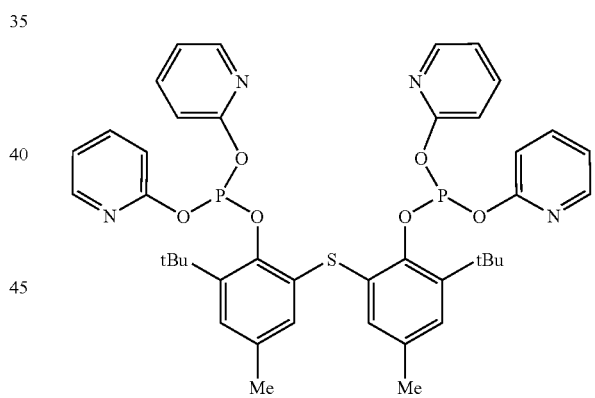
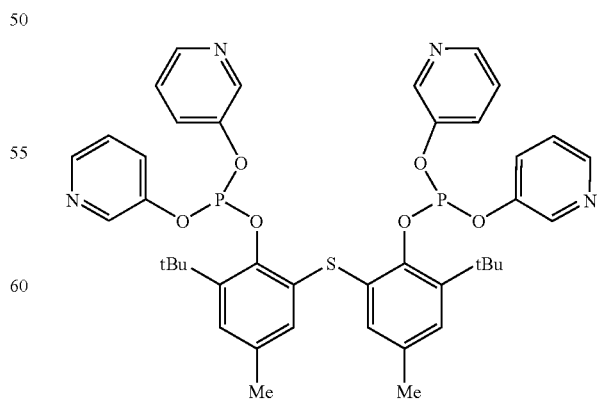

TABLE II-continued
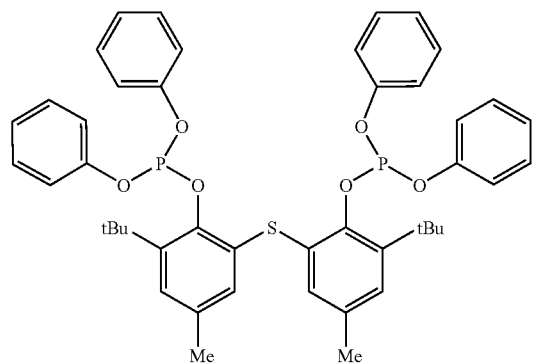
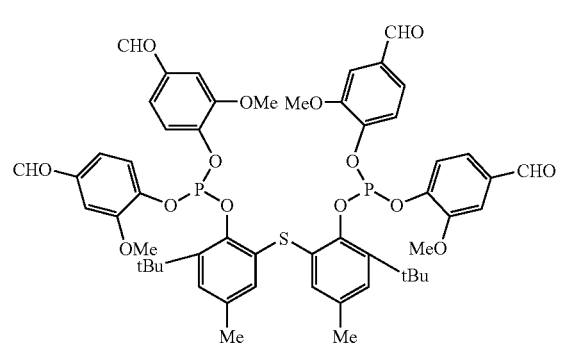
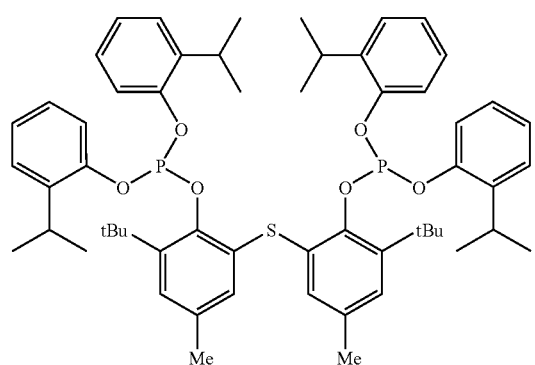
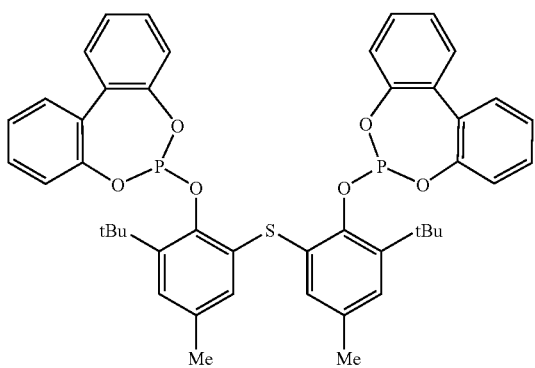
TABLE II-continued
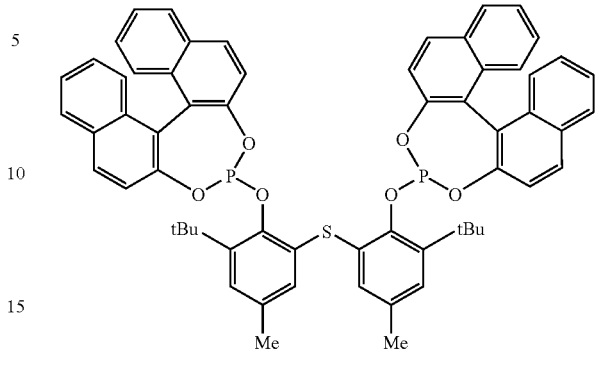
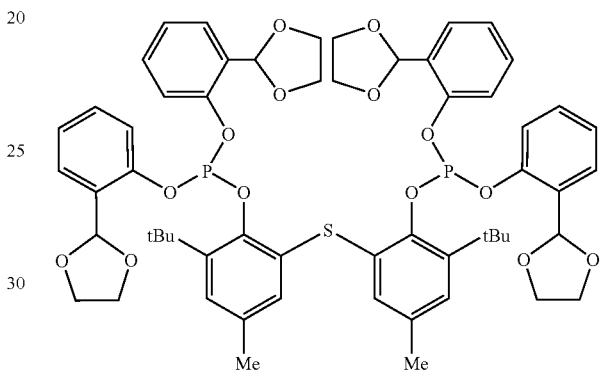
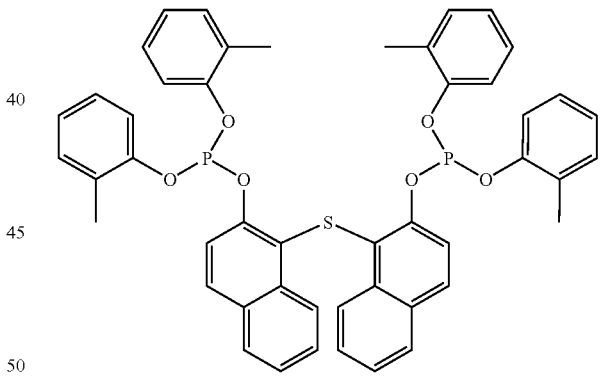
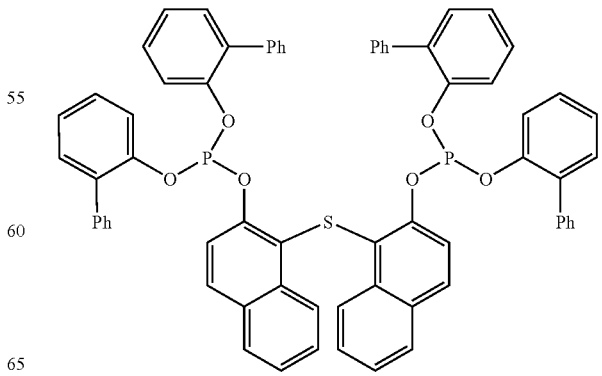

TABLE II-continued
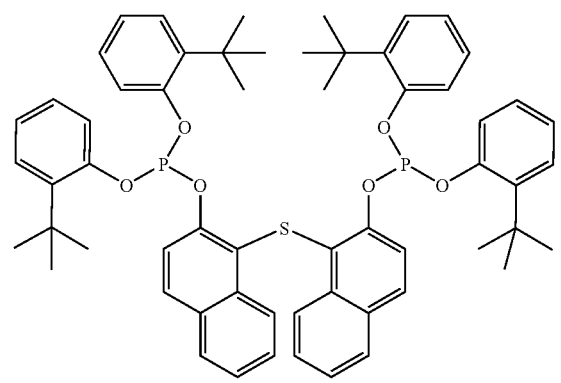
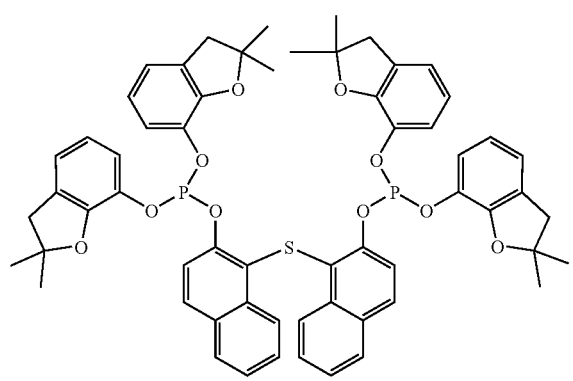
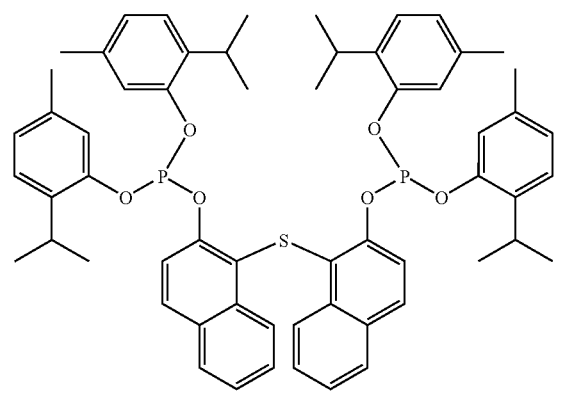
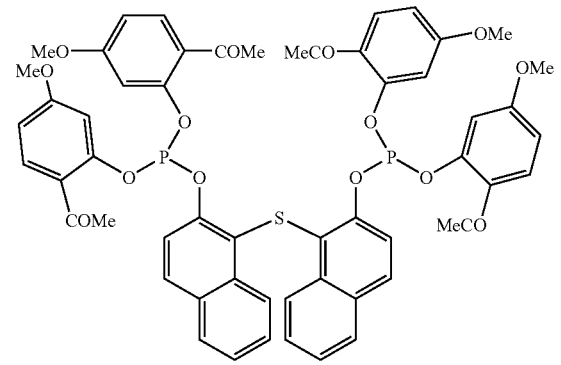
TABLE II-continued
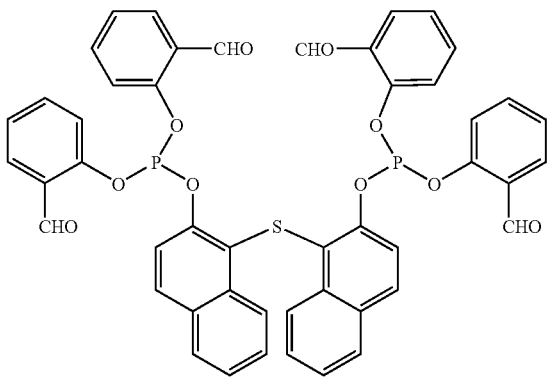
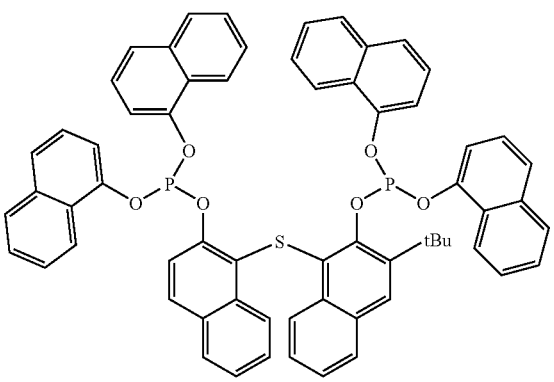
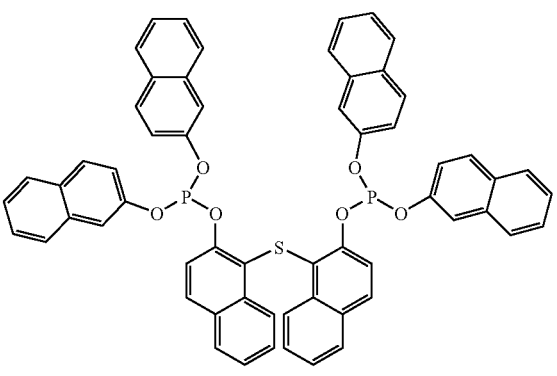
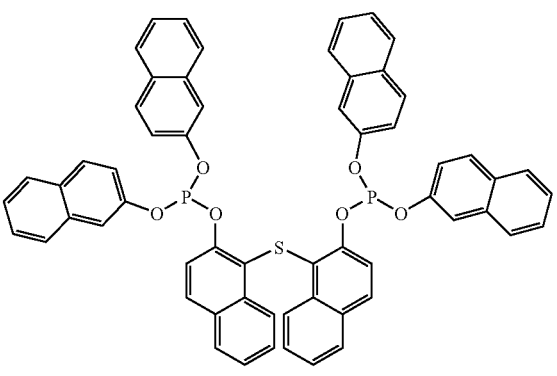

TABLE II-continued
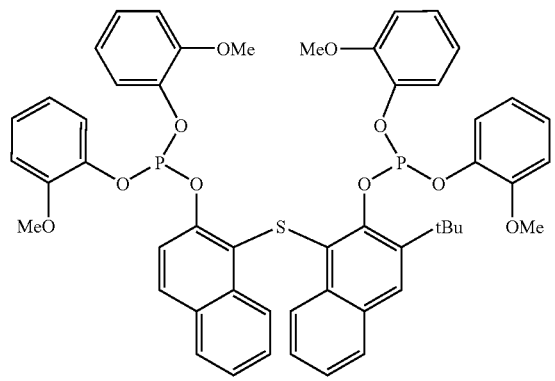
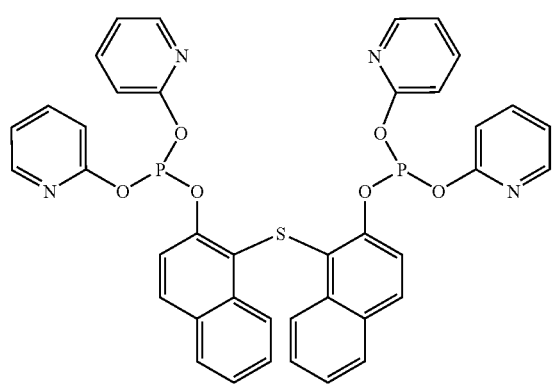
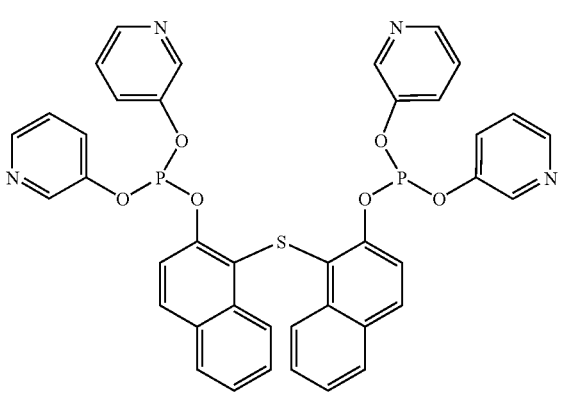
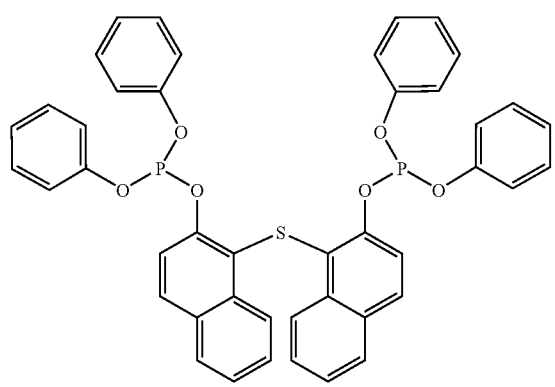
TABLE II-continued
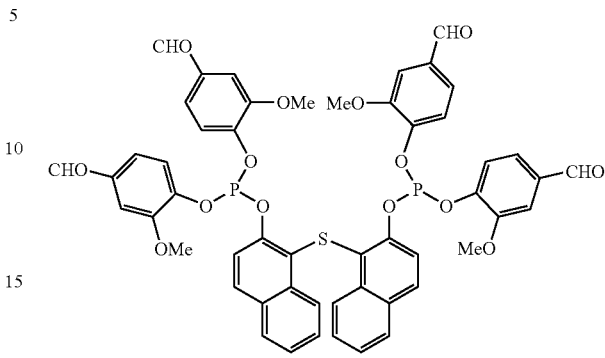
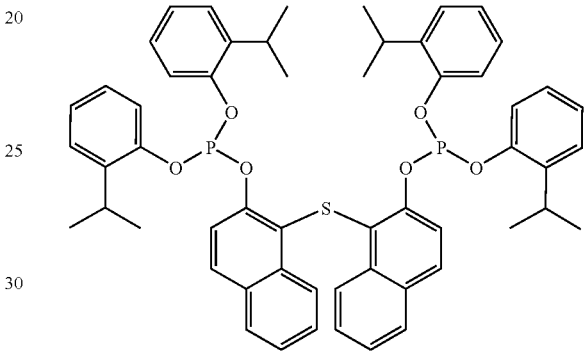
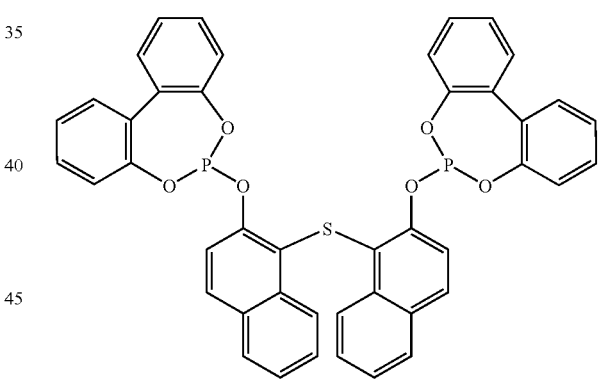
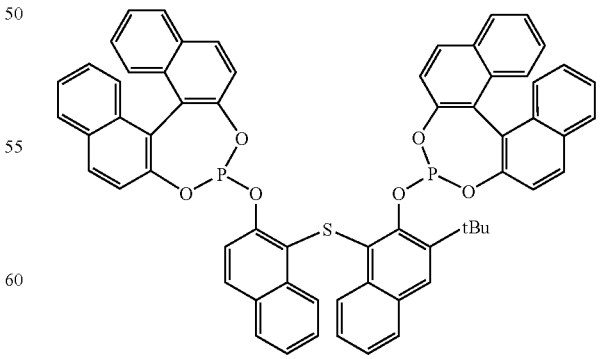

TABLE II-continued
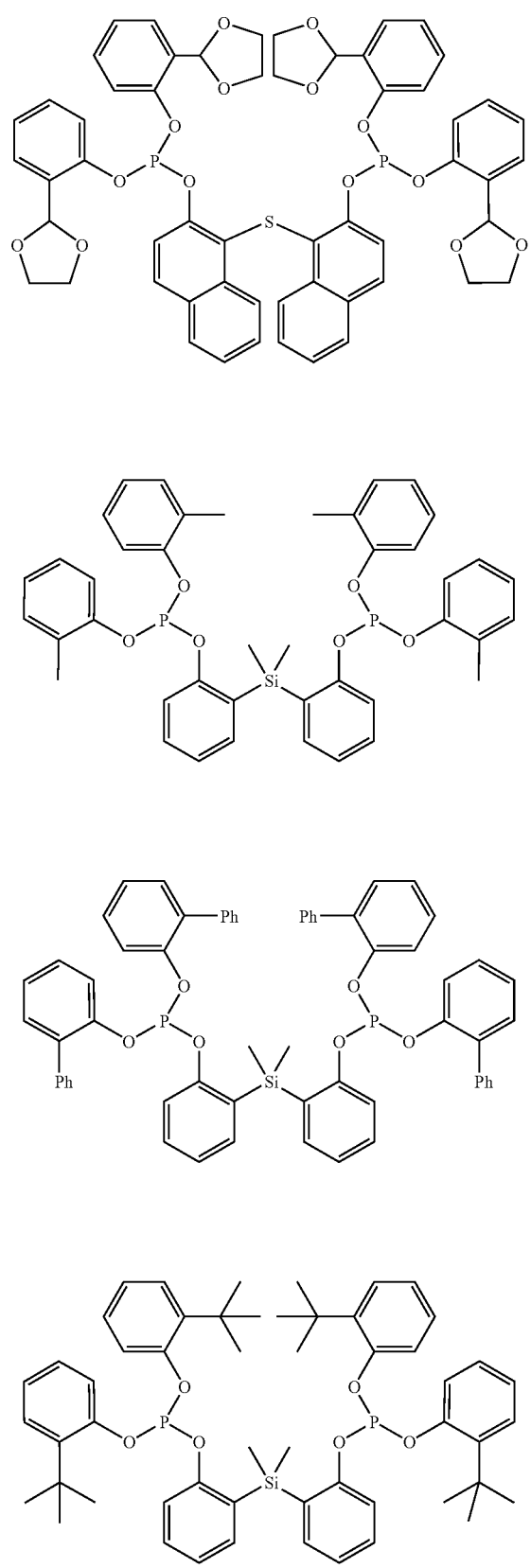
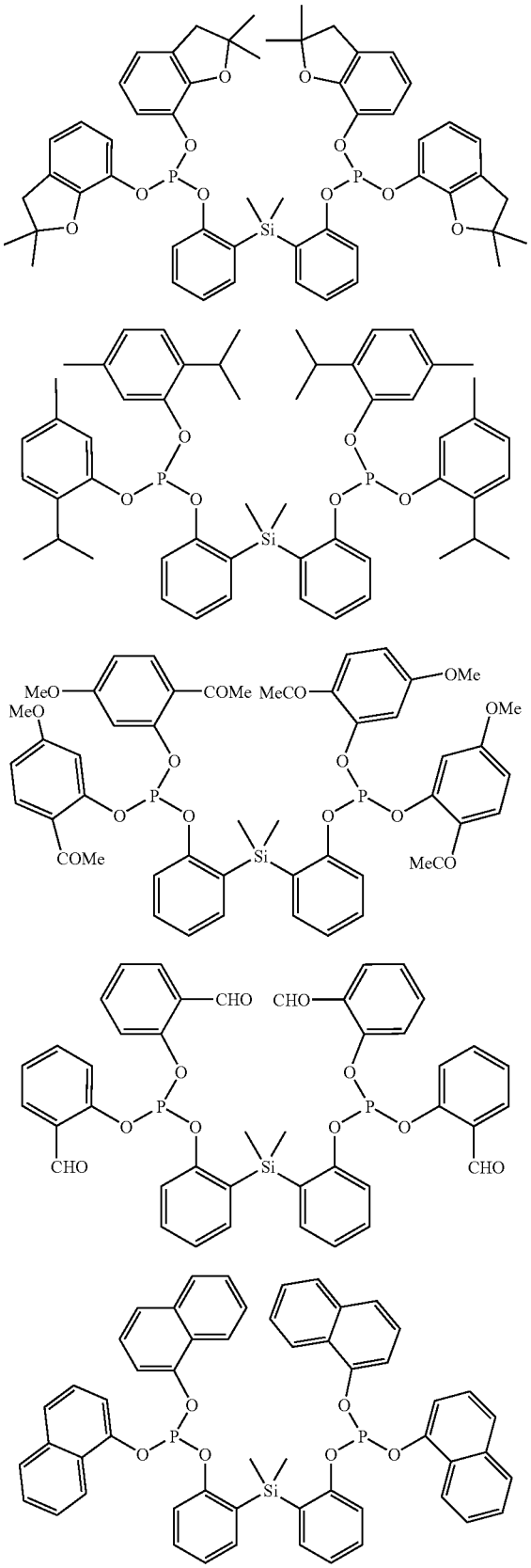

TABLE II-continued
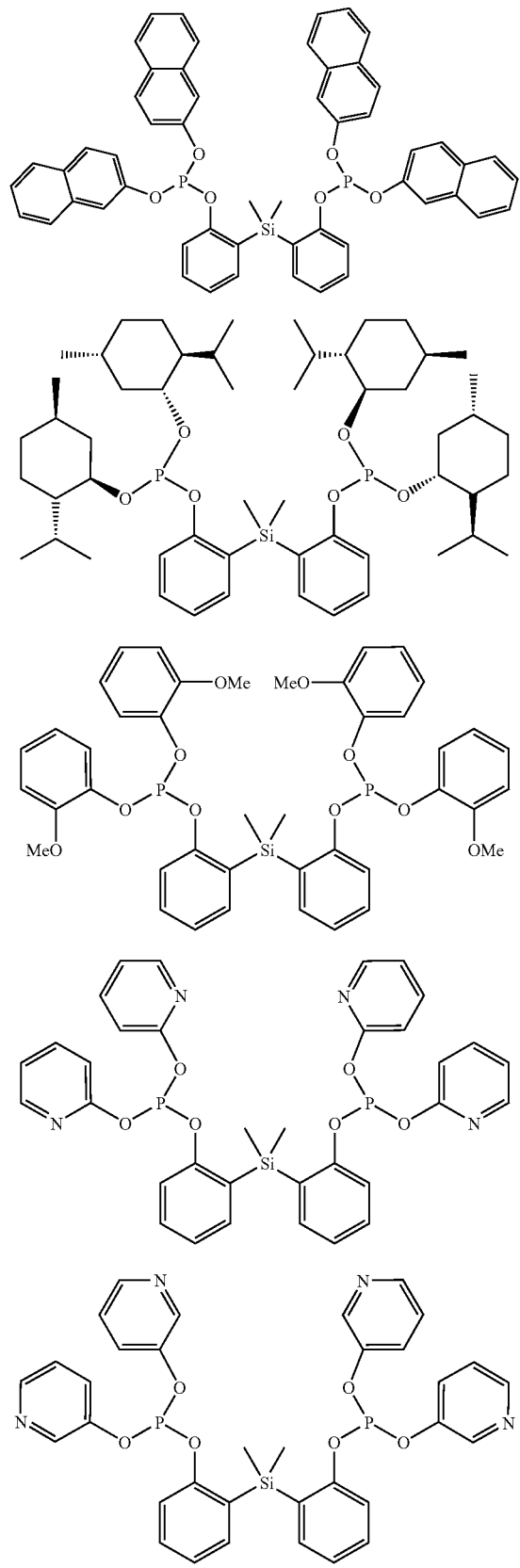
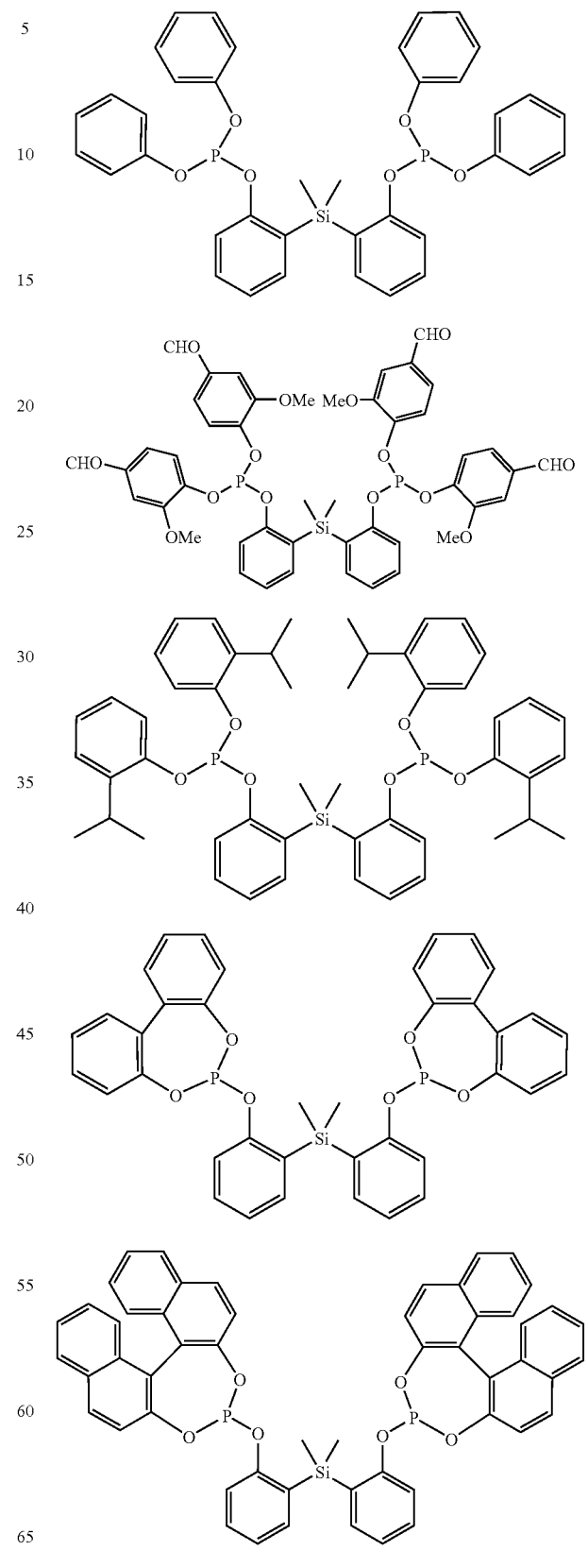

TABLE II-continued
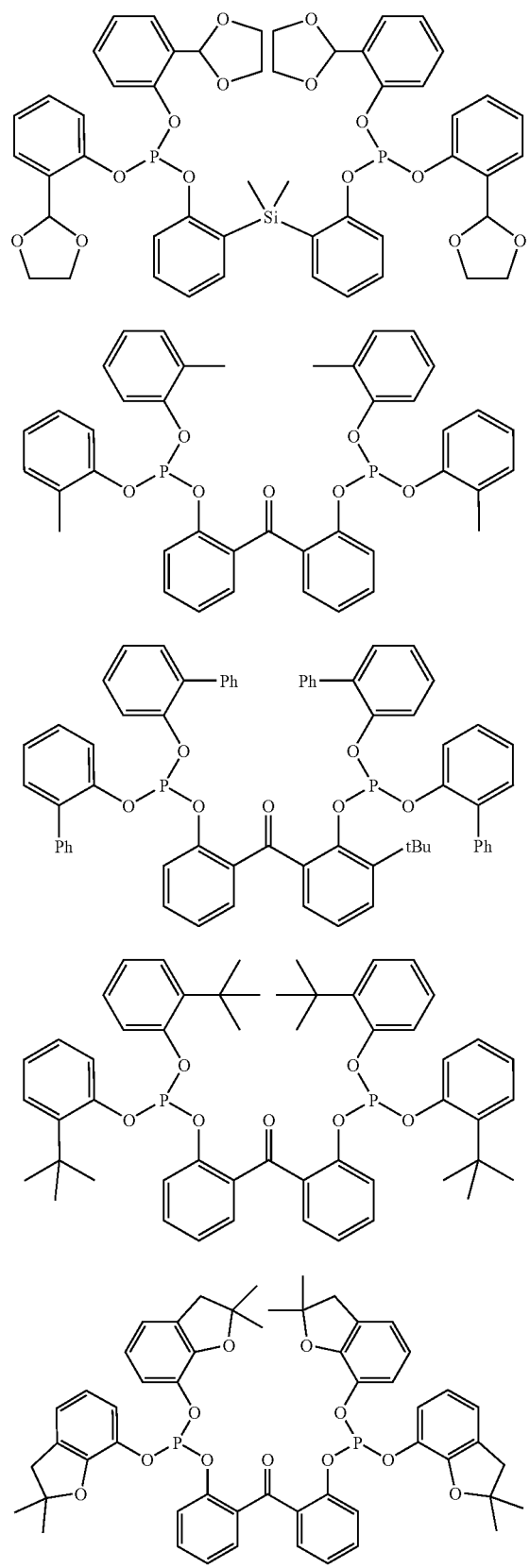
TABLE II-continued
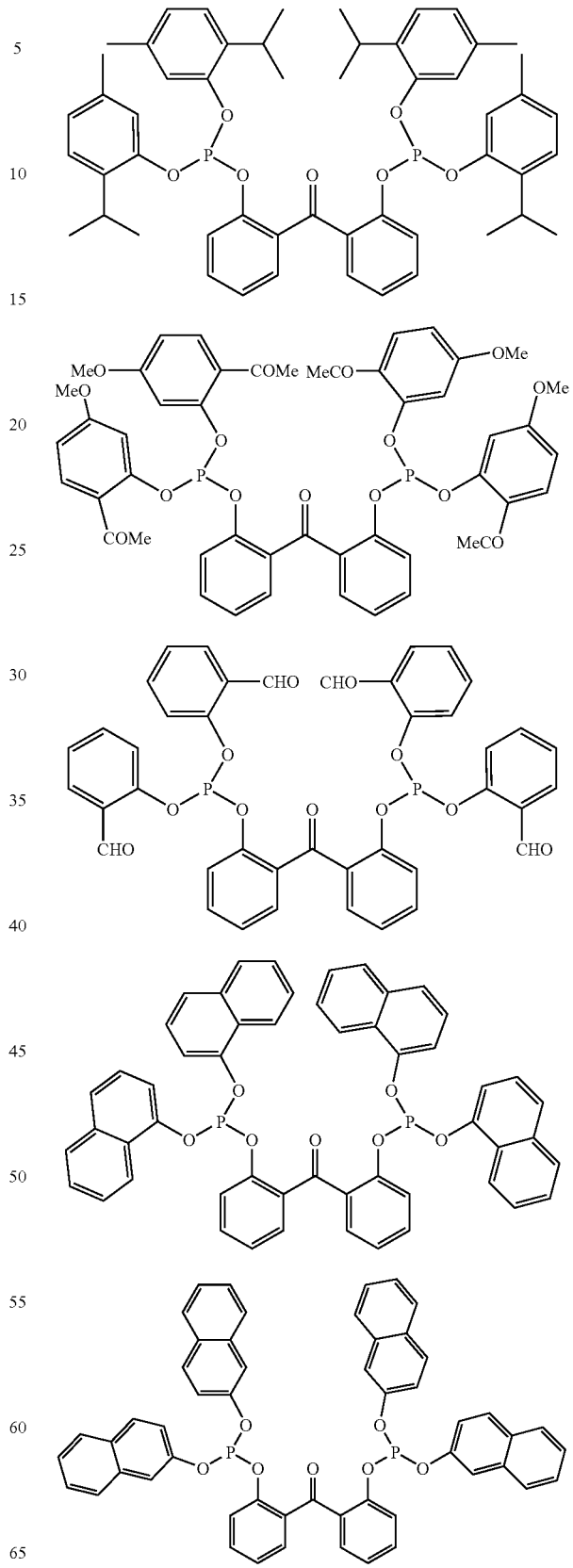

TABLE II-continued
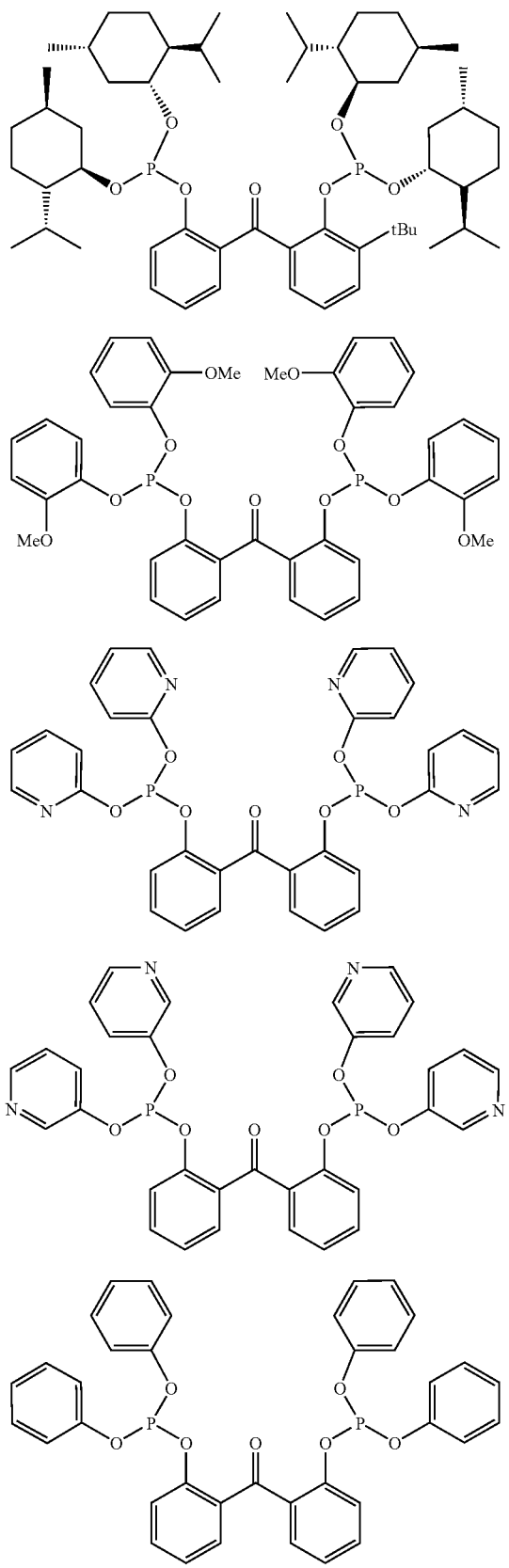
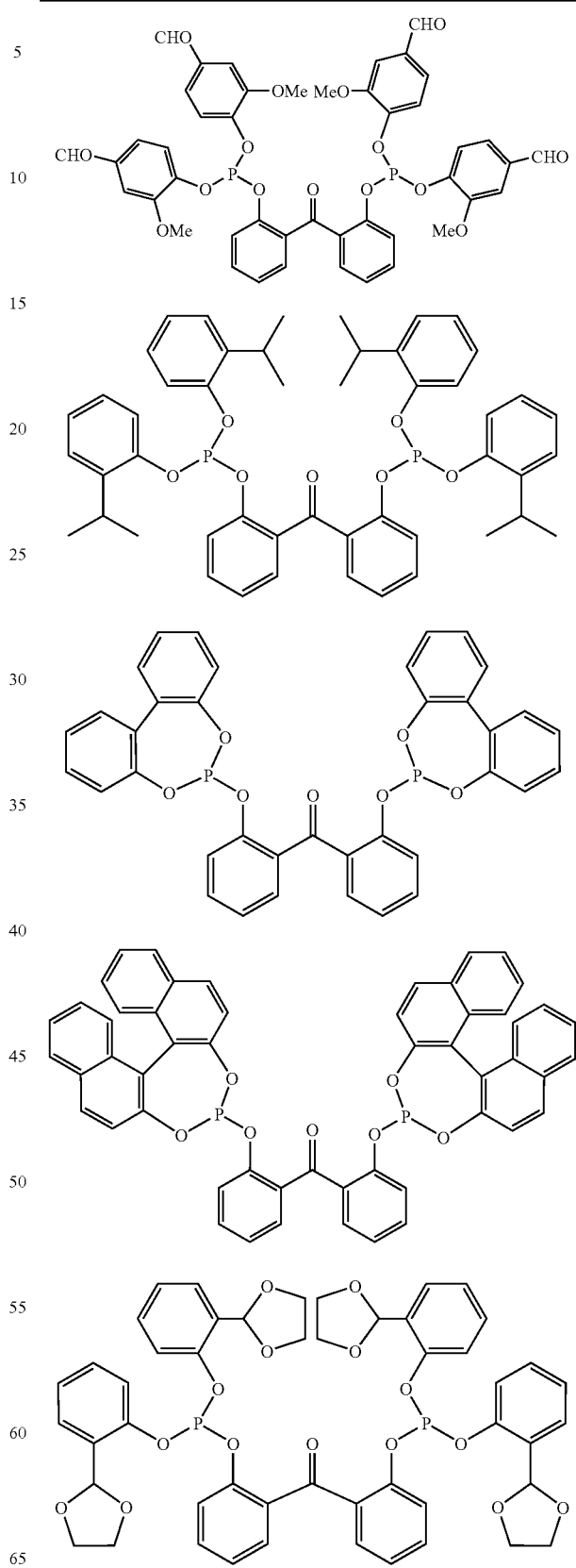

TABLE II-continued
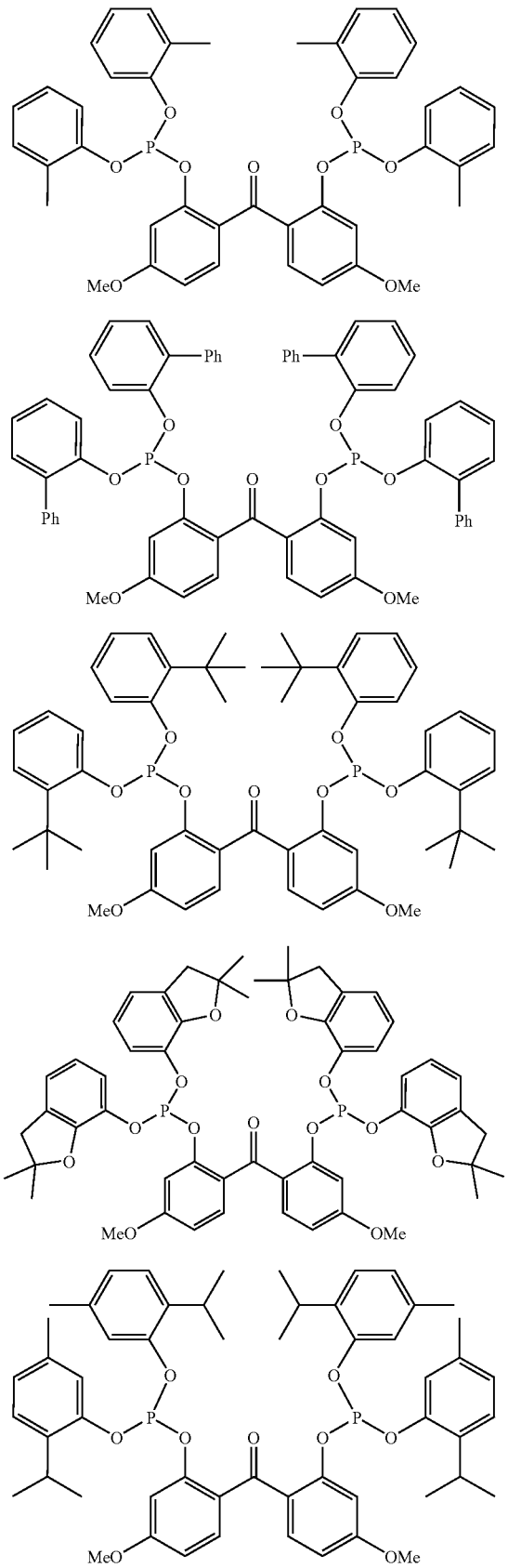
TABLE II-continued
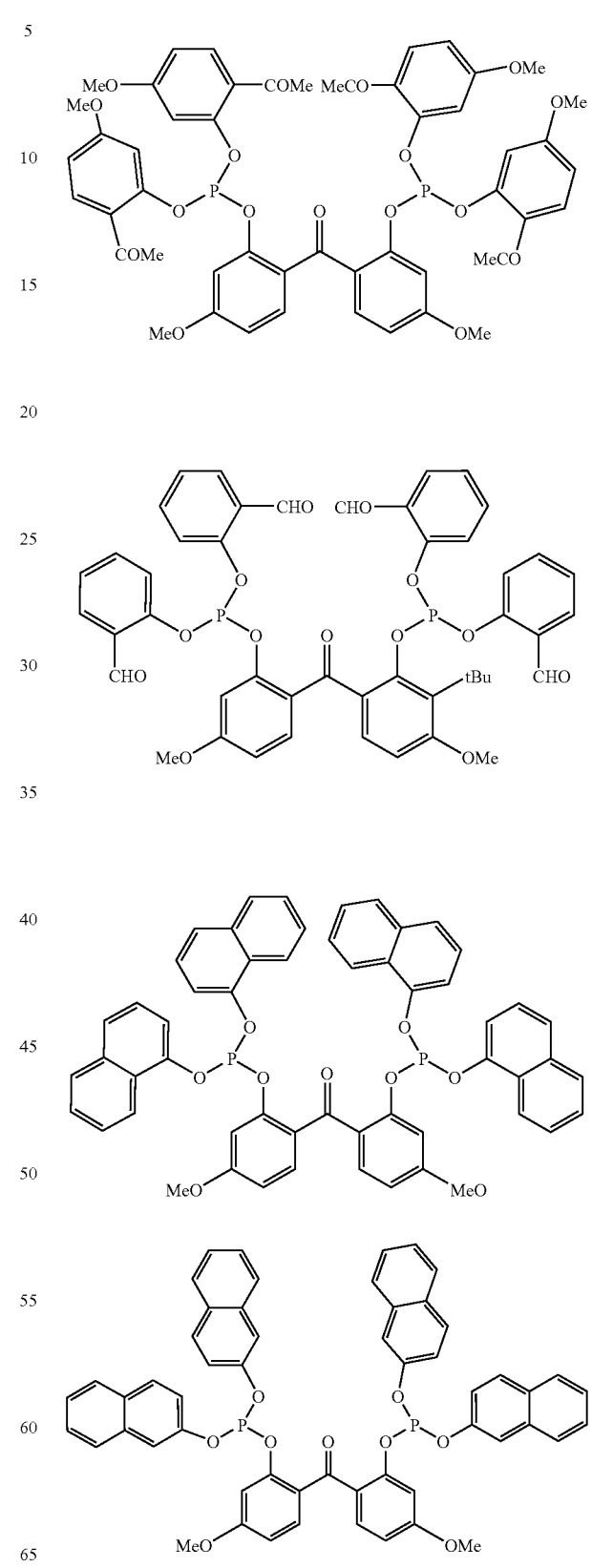

TABLE II-continued
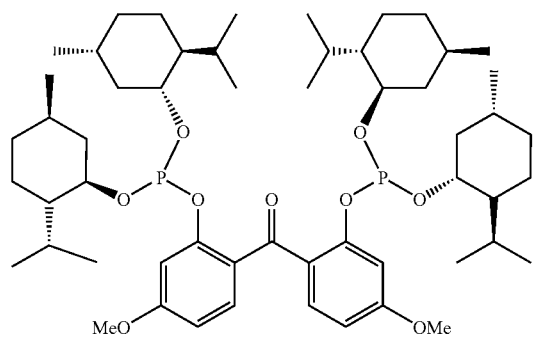
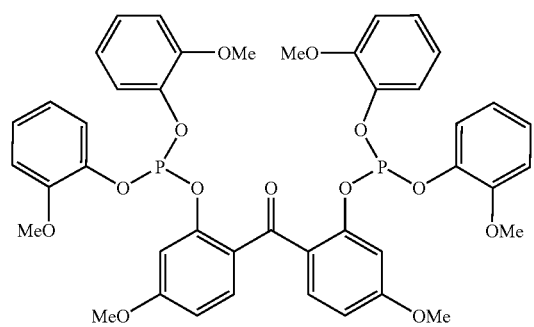
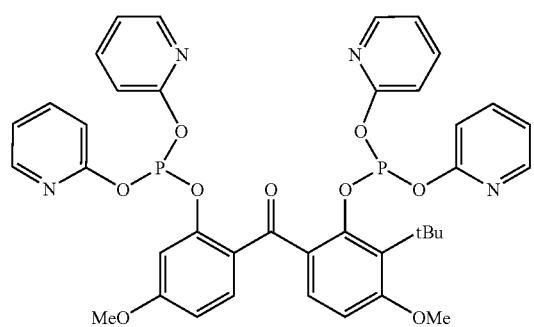
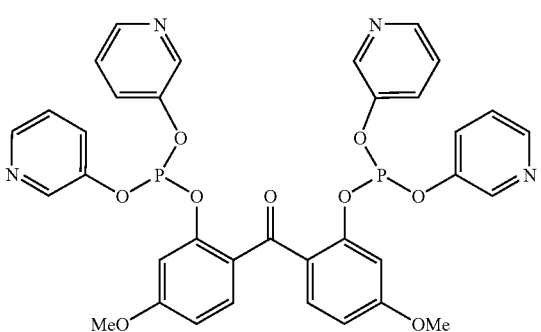
TABLE II-continued
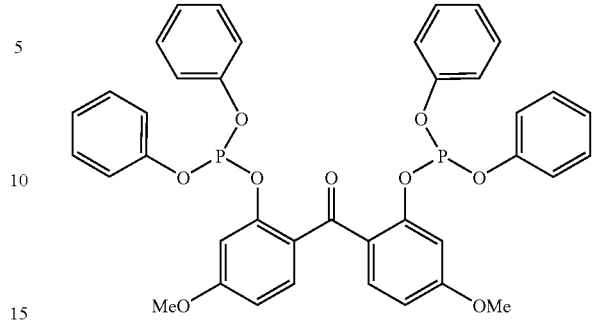
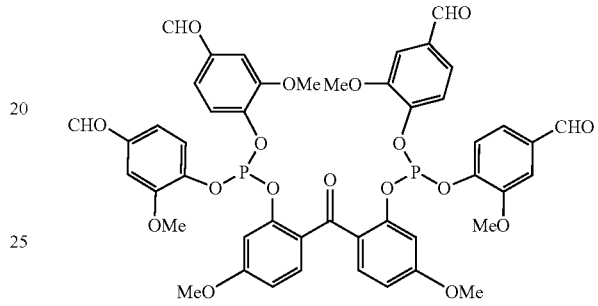
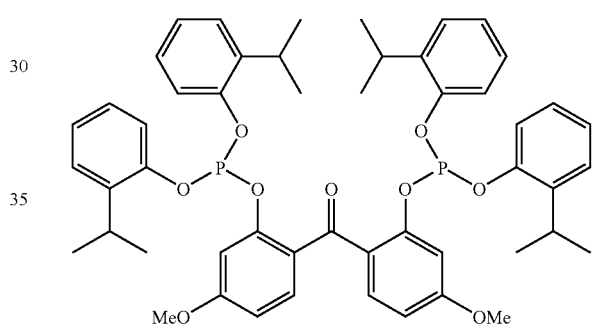
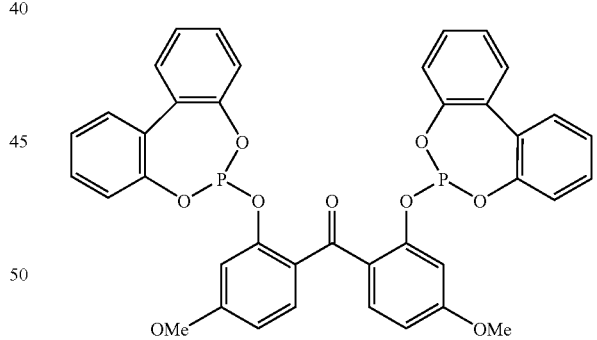
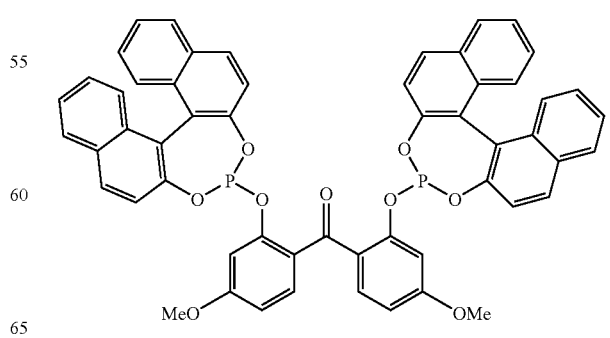

TABLE II-continued
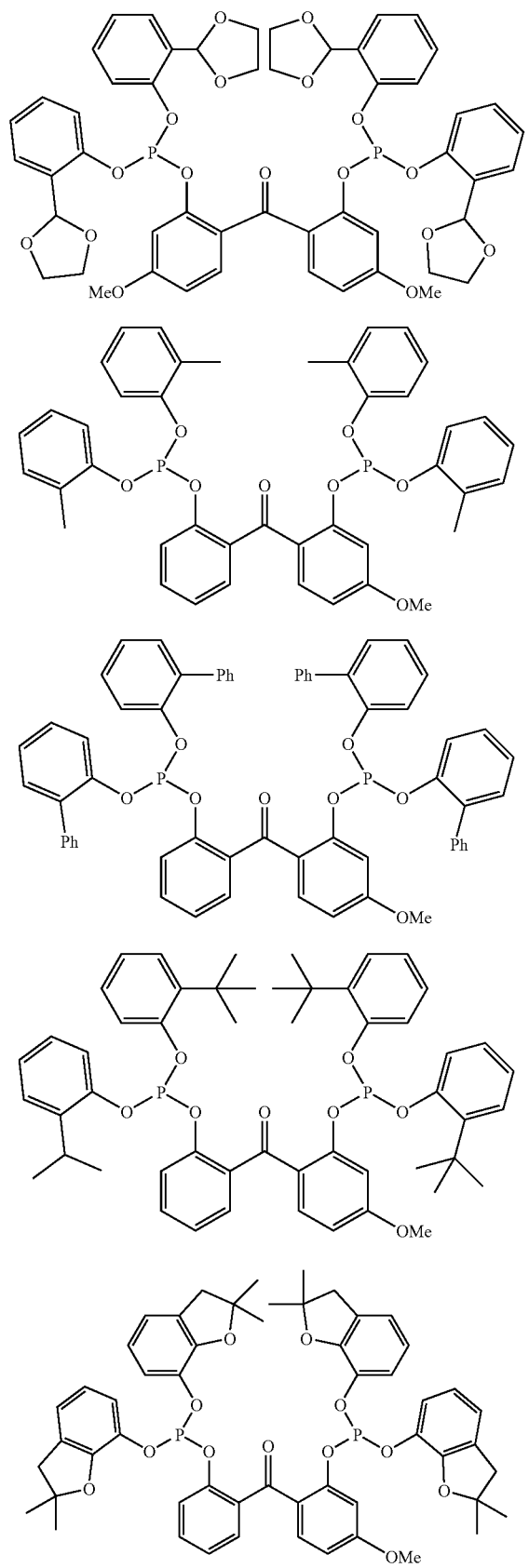
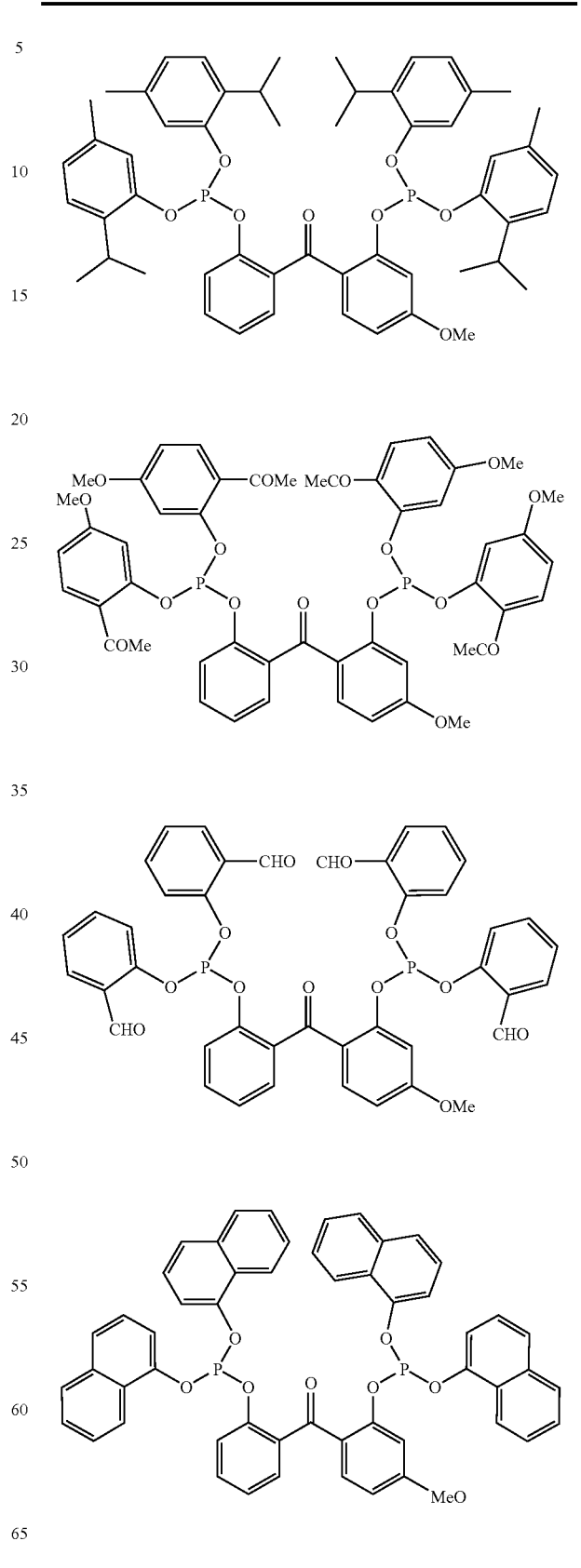

TABLE II-continued
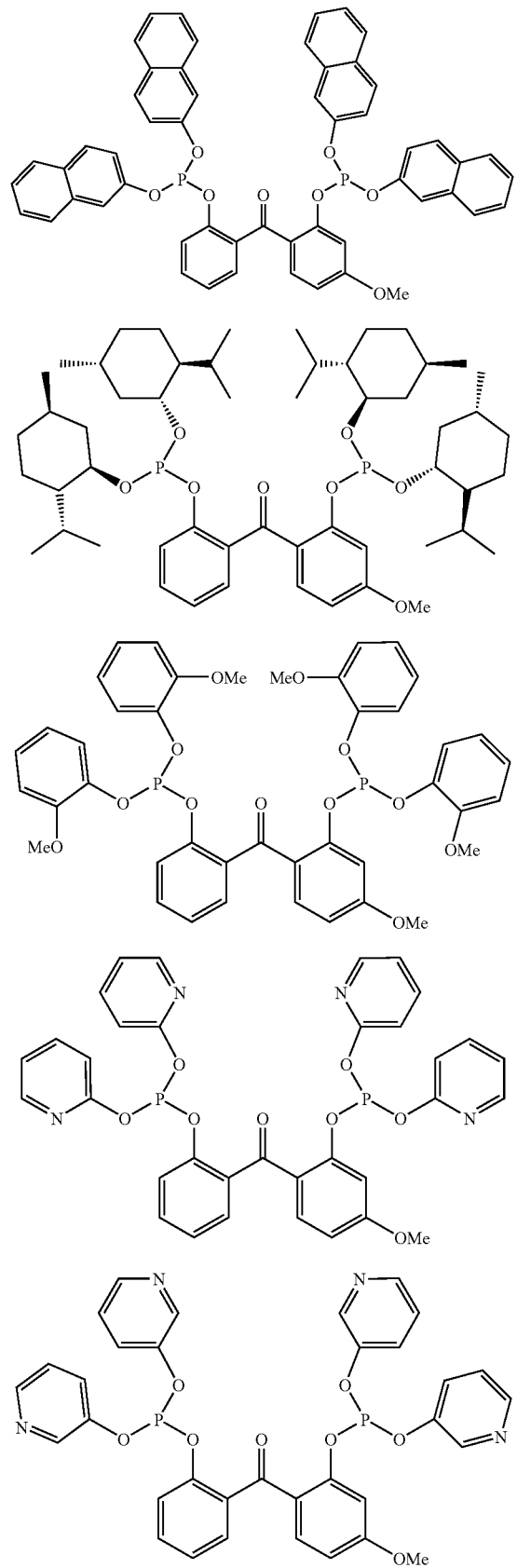
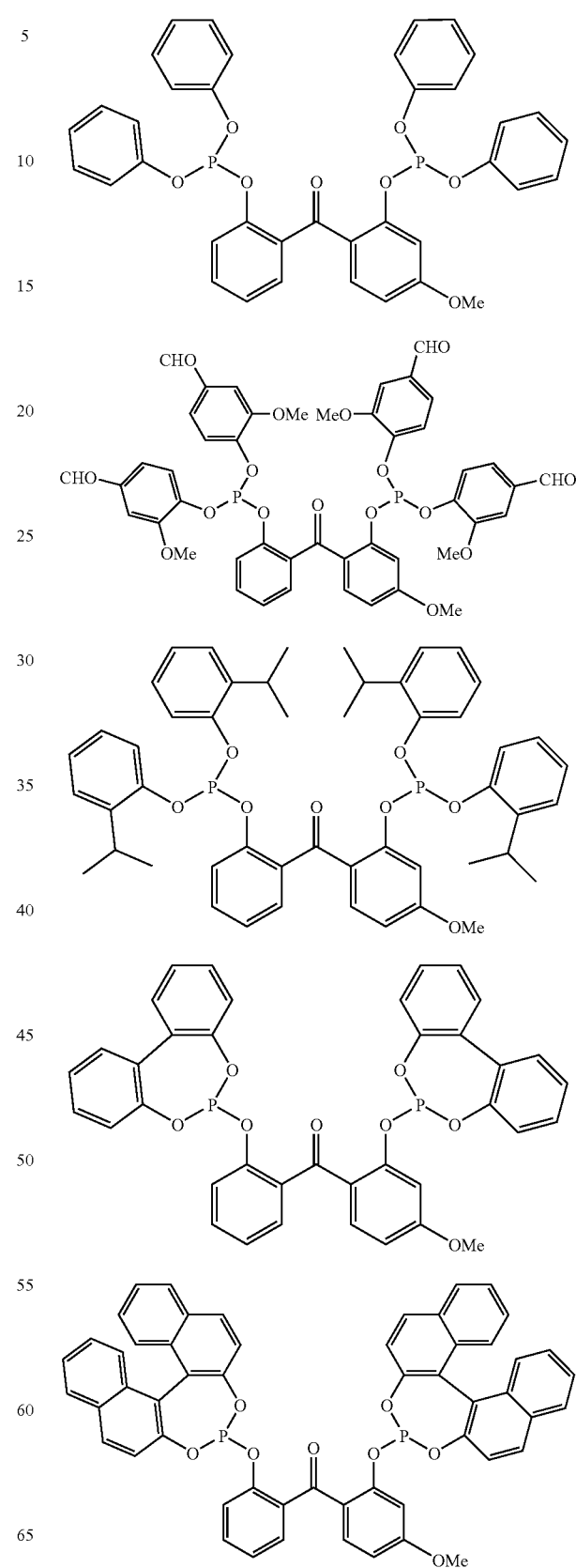

TABLE II-continued
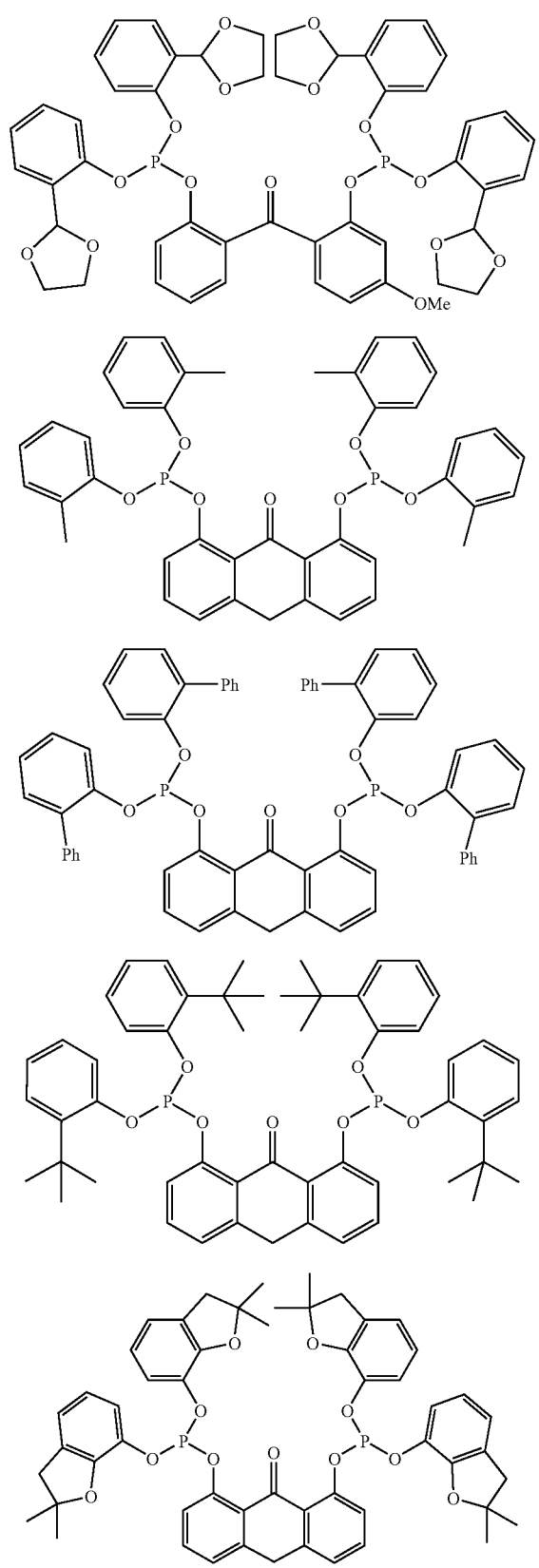
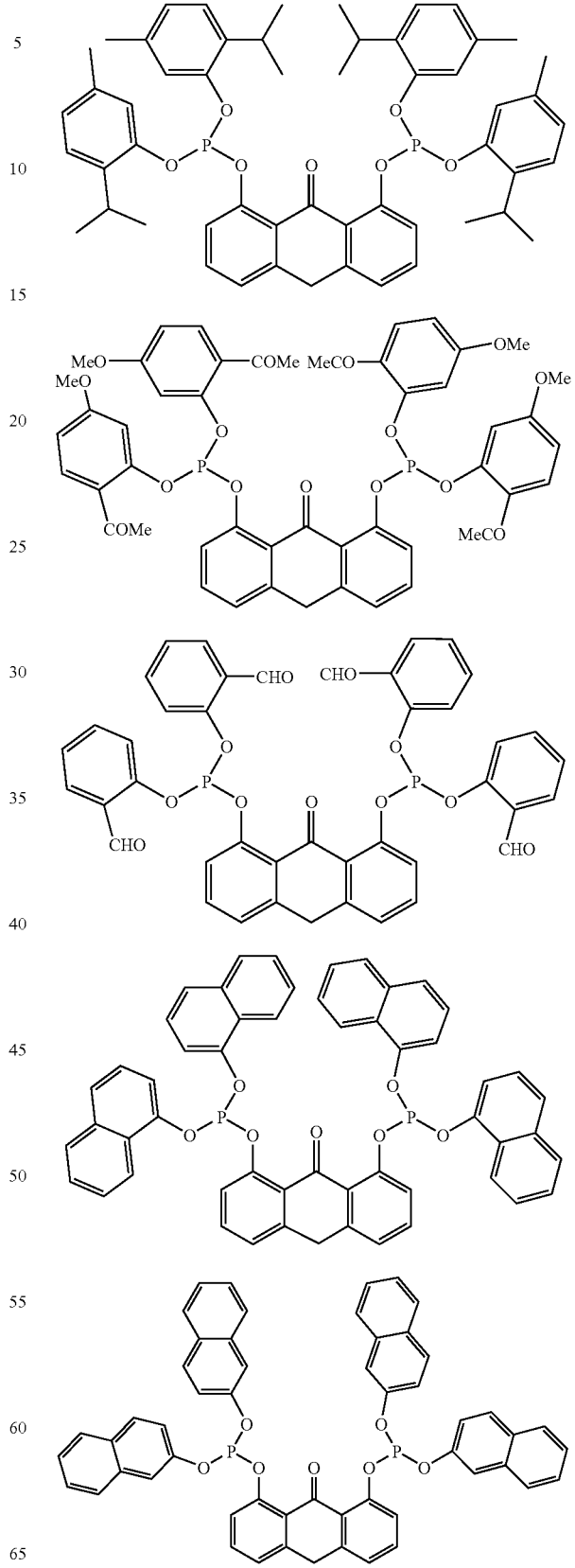

TABLE II-continued
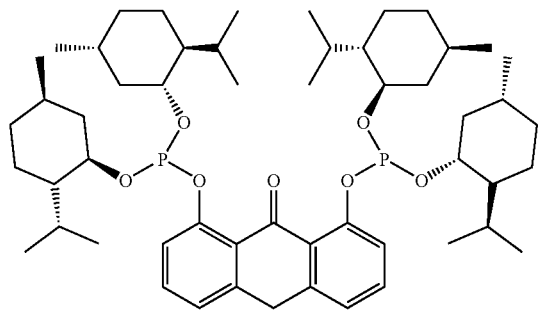
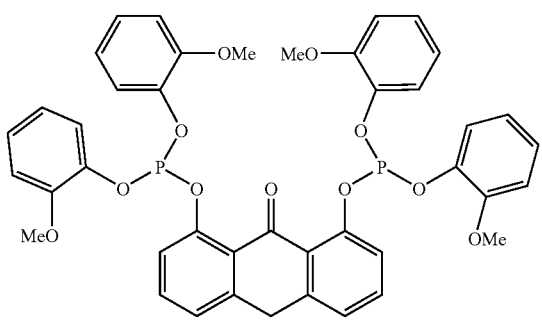
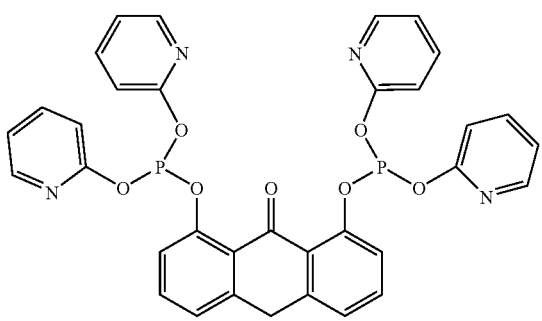
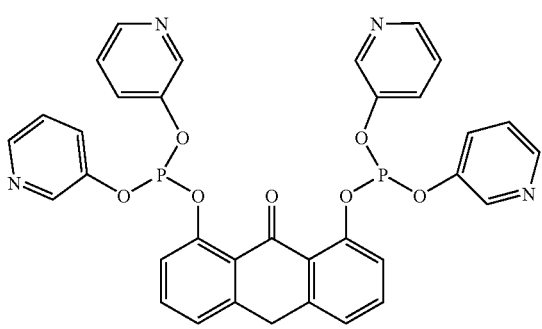
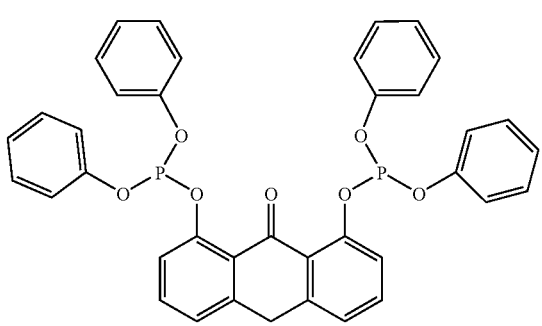
TABLE II-continued
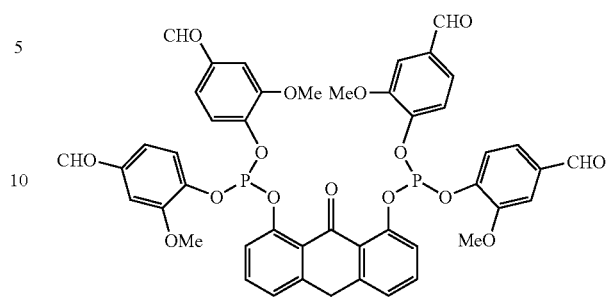
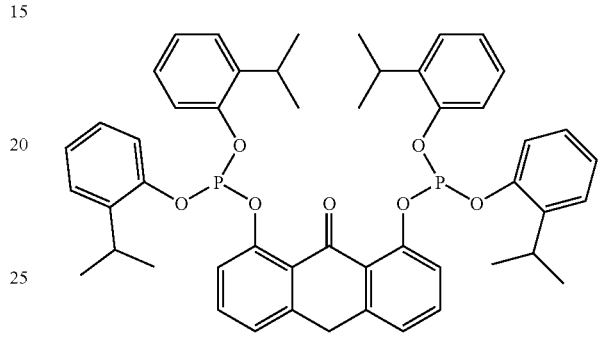
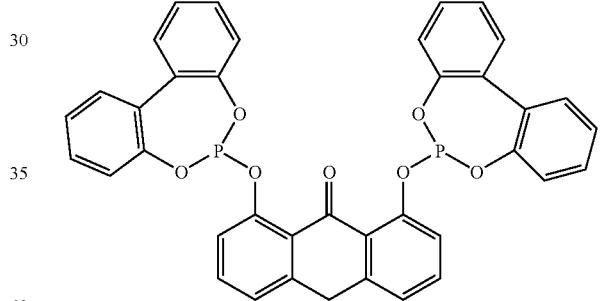
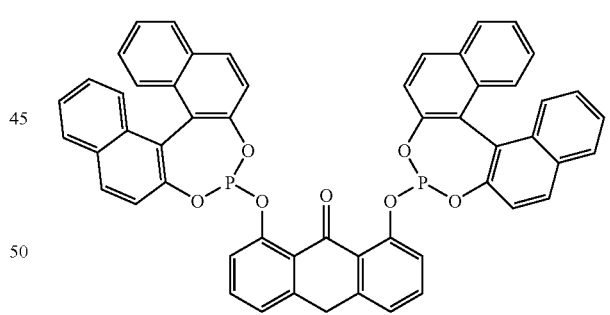
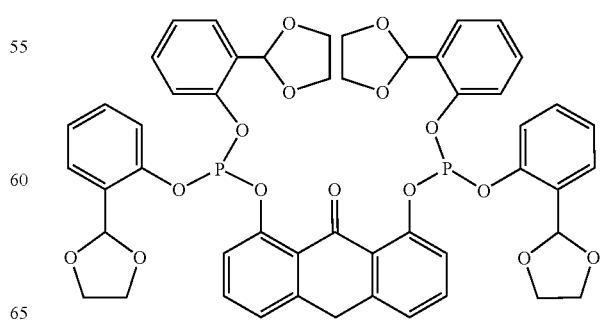

TABLE II-continued
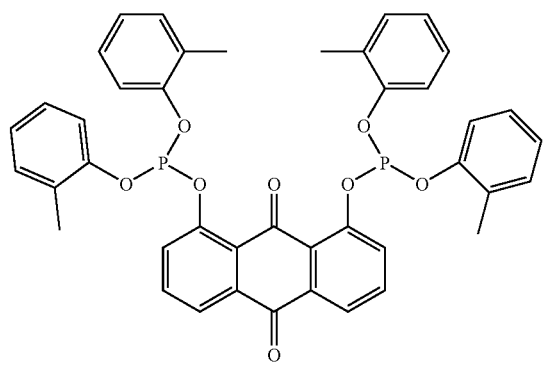
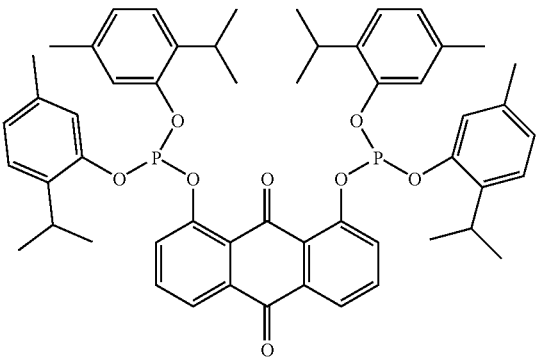
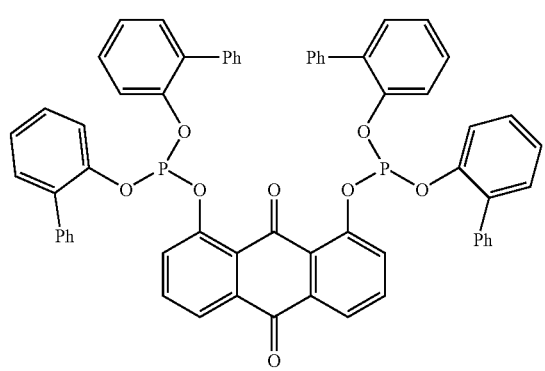
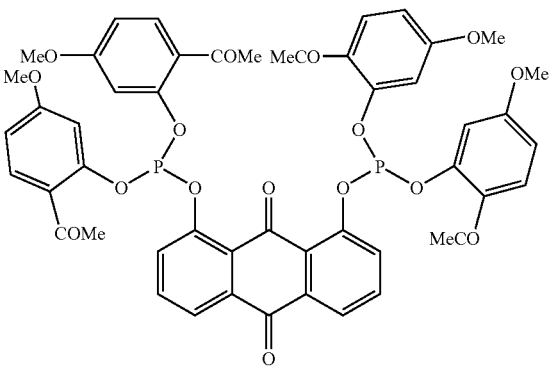
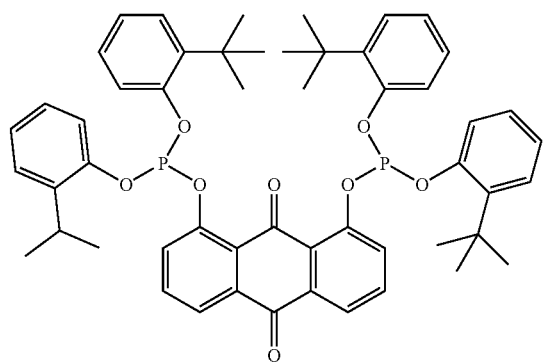
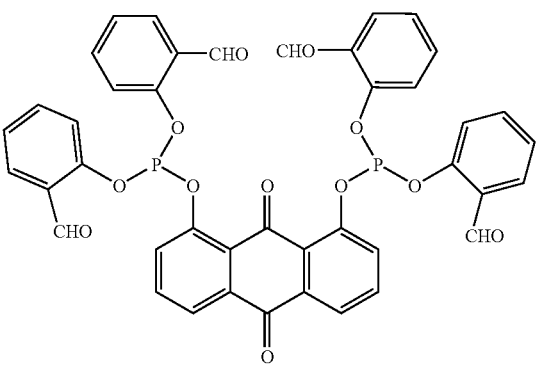
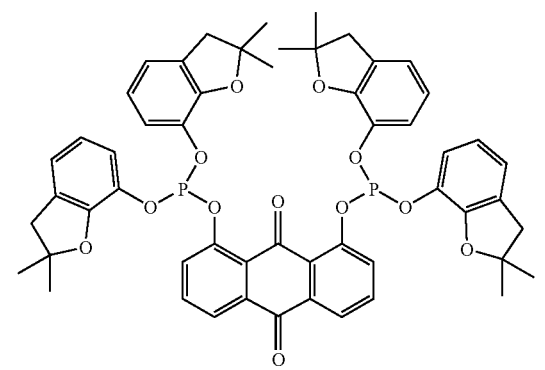
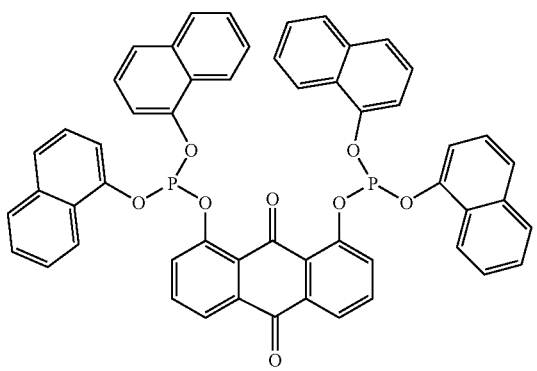

TABLE II-continued
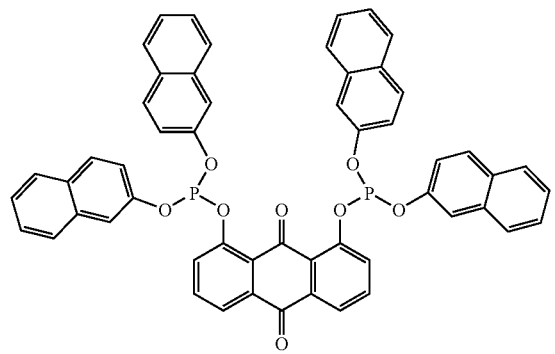
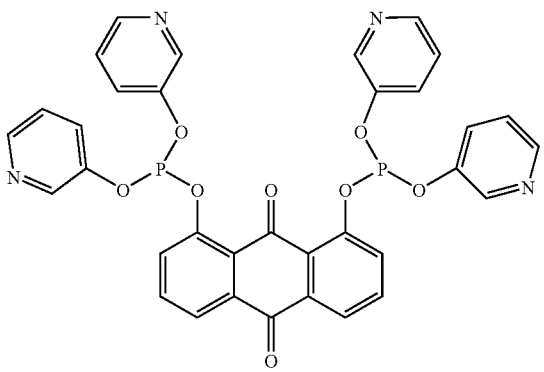
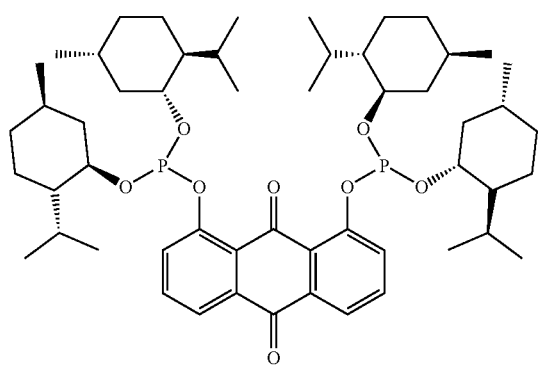
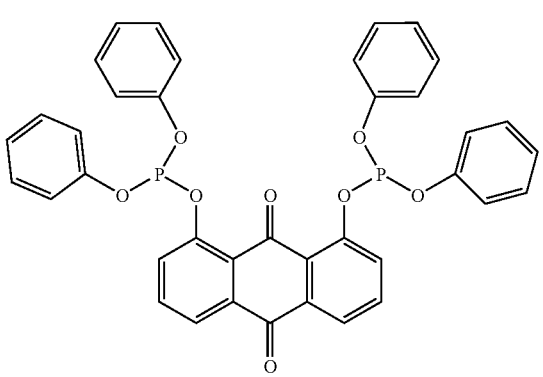
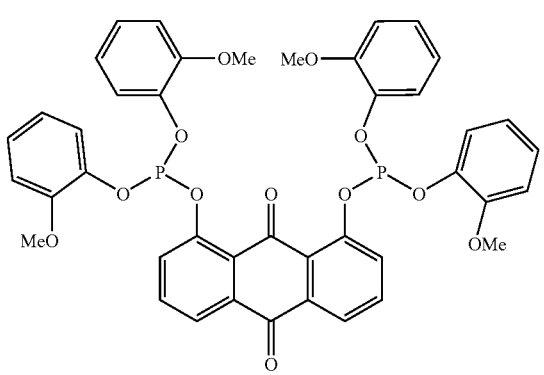
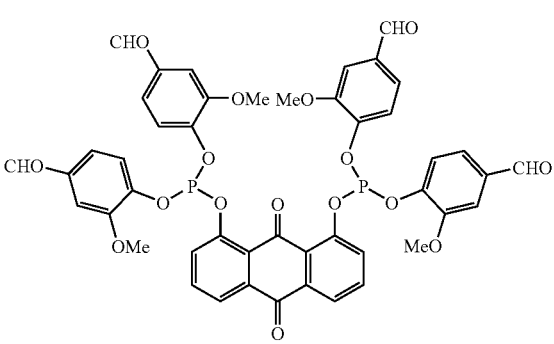
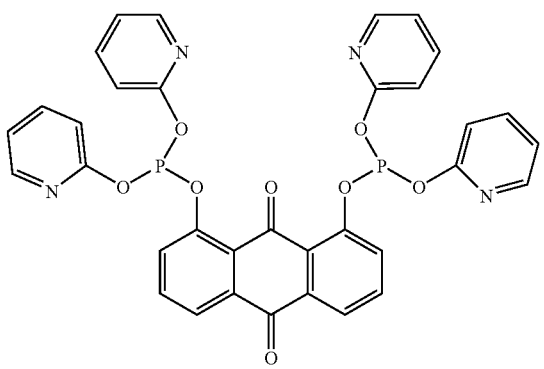
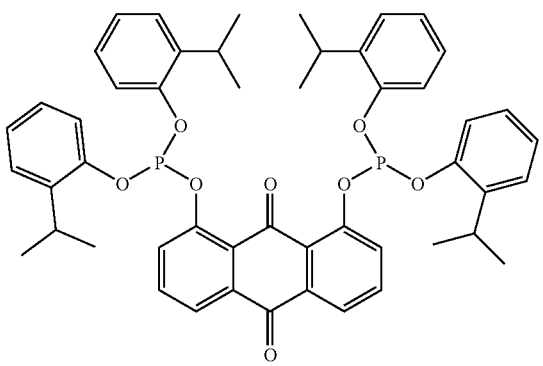

TABLE II-continued
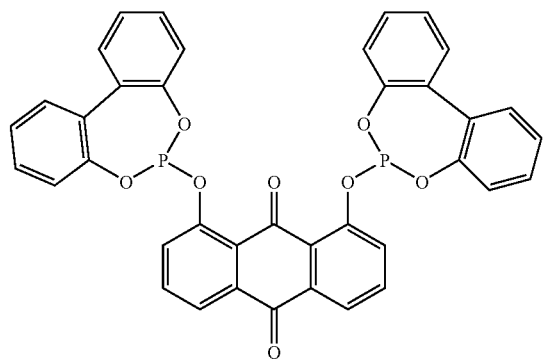
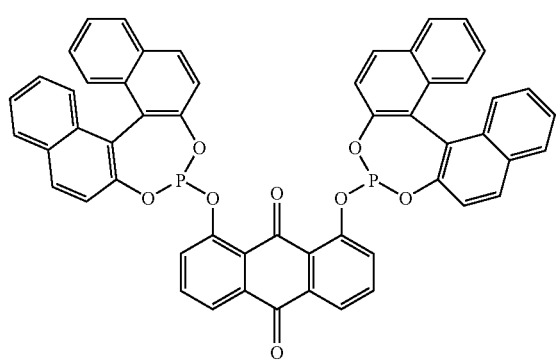
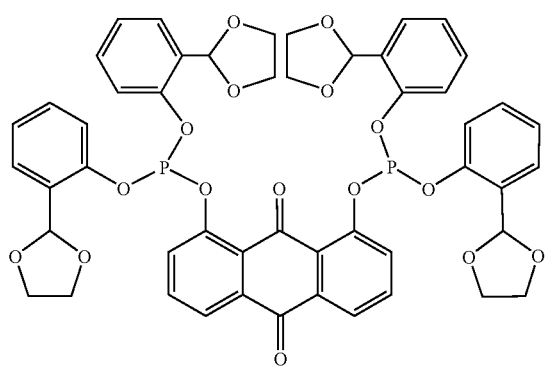
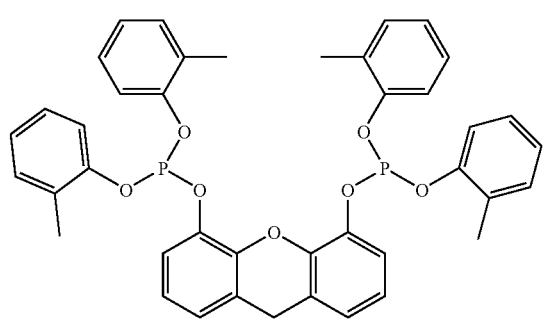
TABLE II-continued
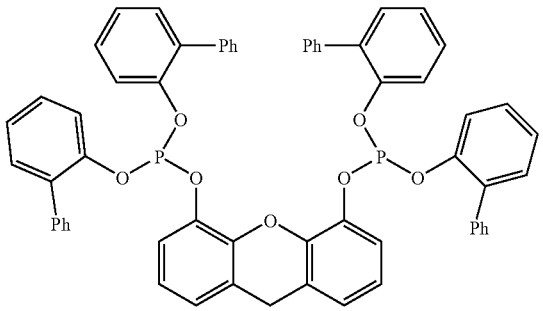
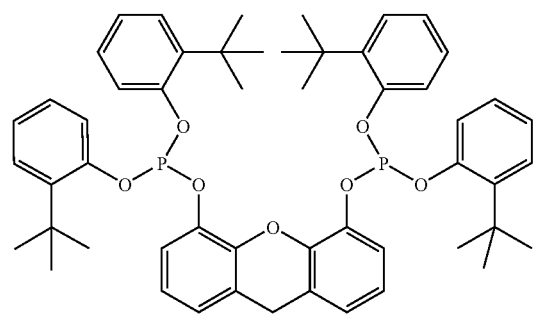
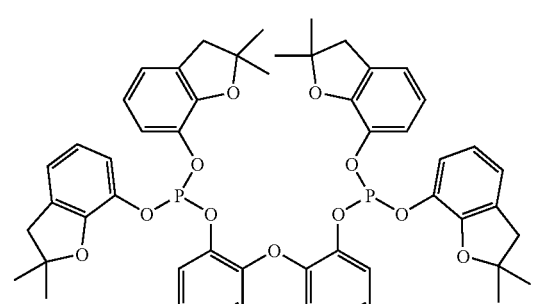
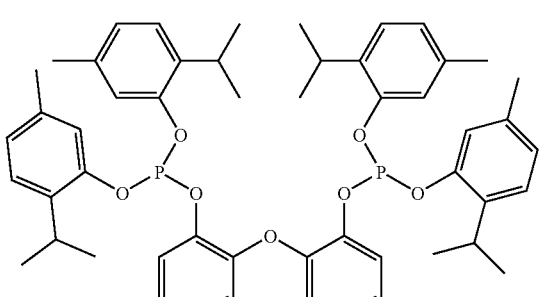
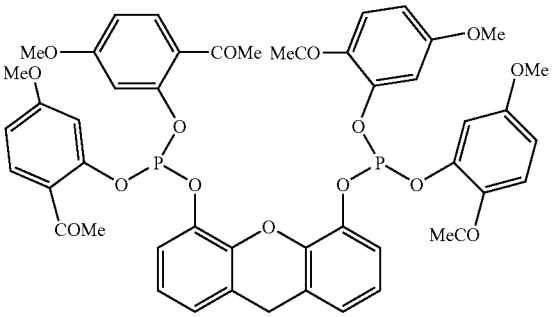

TABLE II-continued
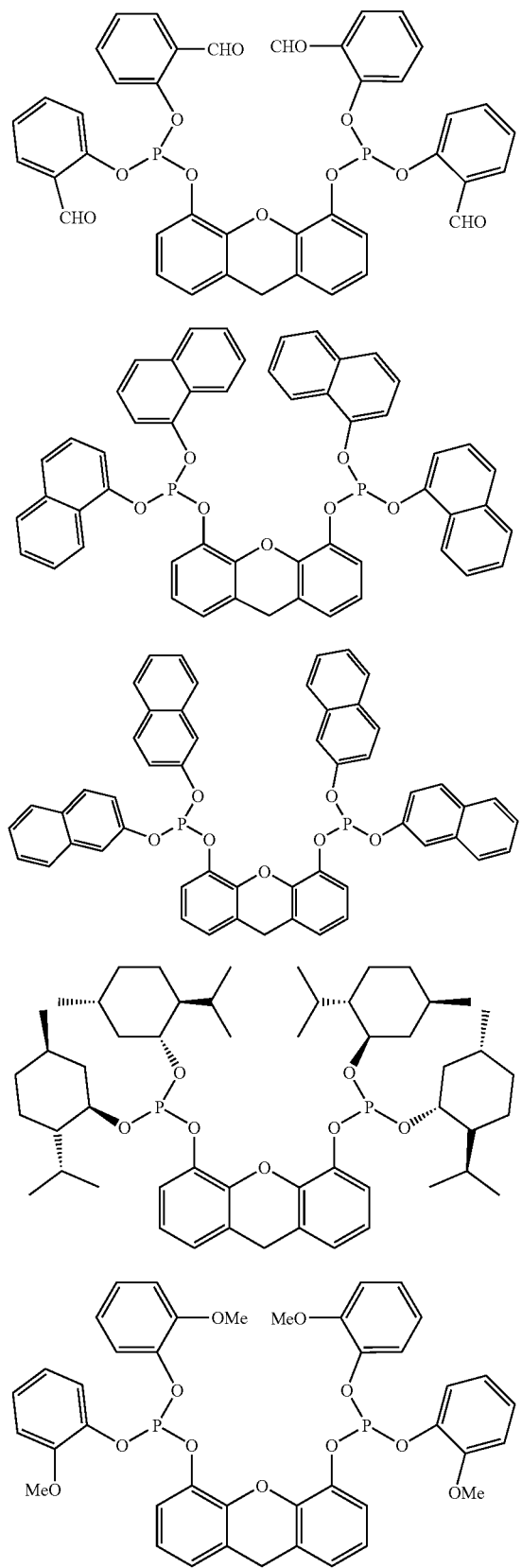
TABLE II-continued
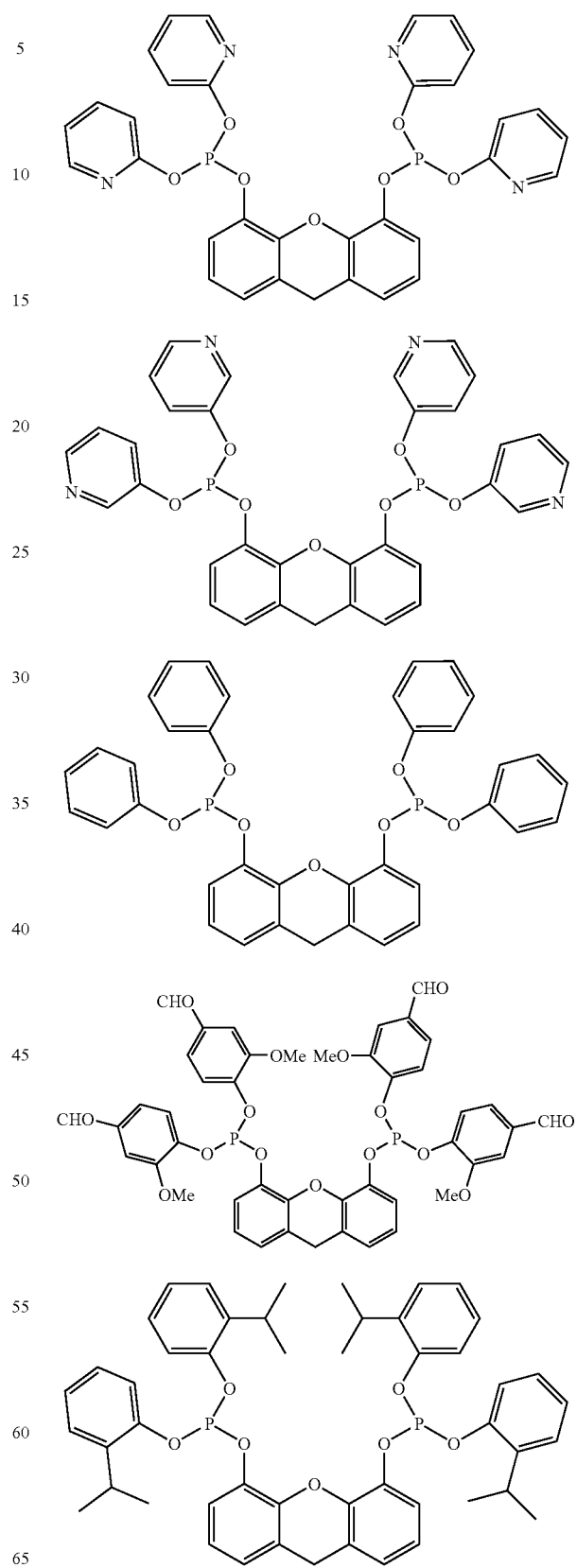

TABLE II-continued
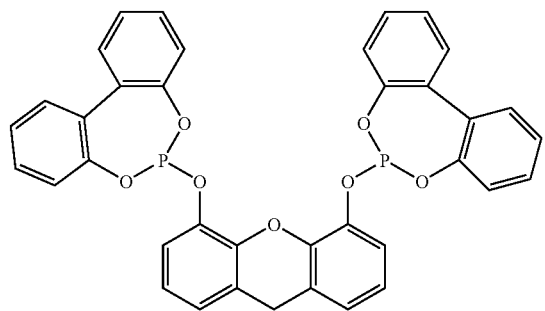
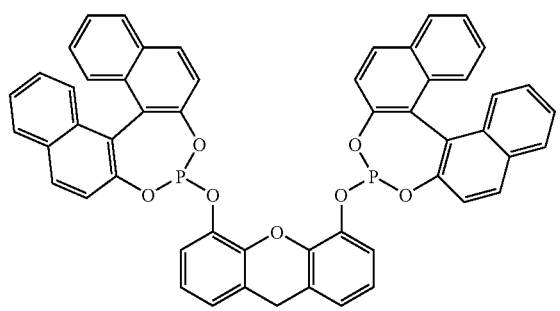
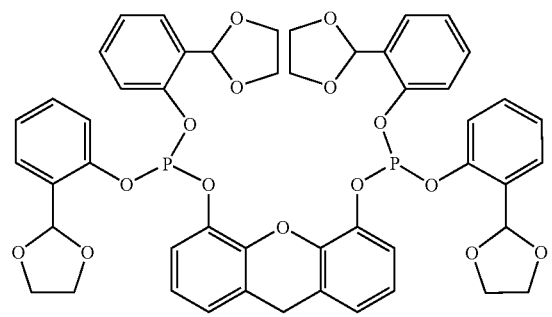
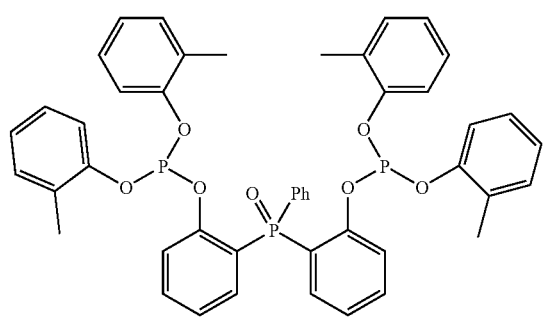
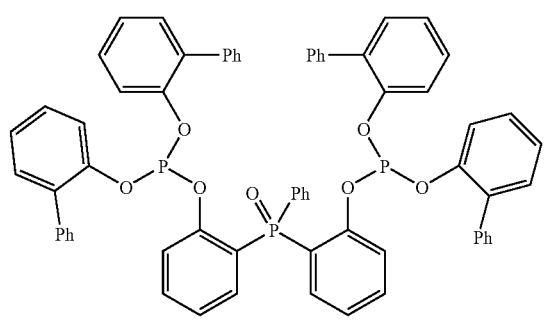
TABLE II-continued
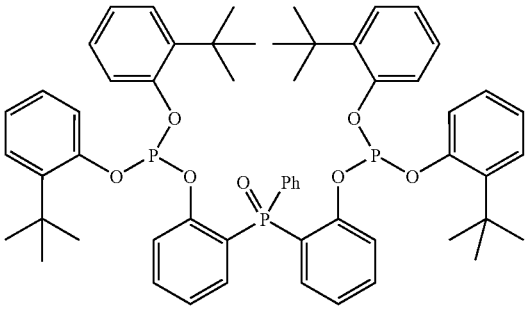
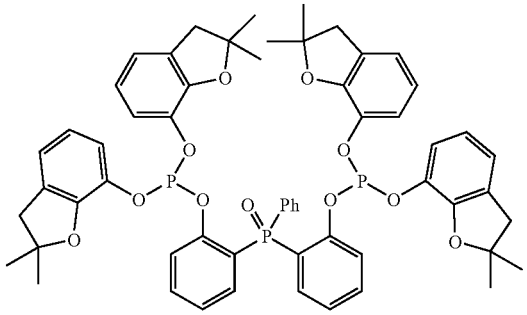
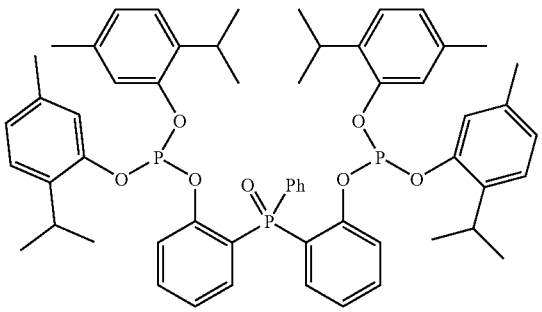
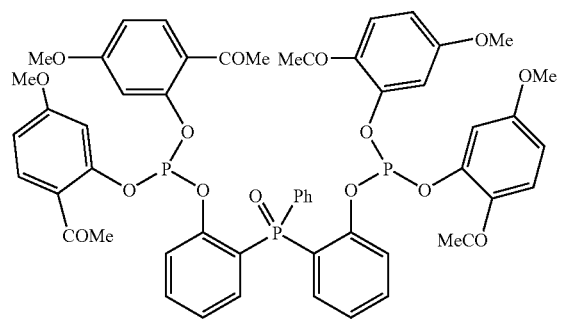
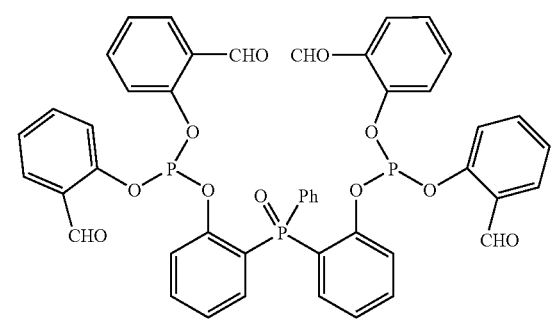

TABLE II-continued
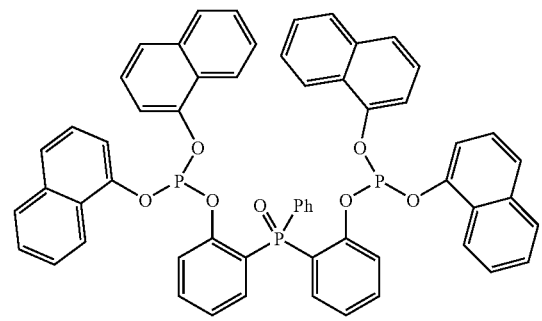
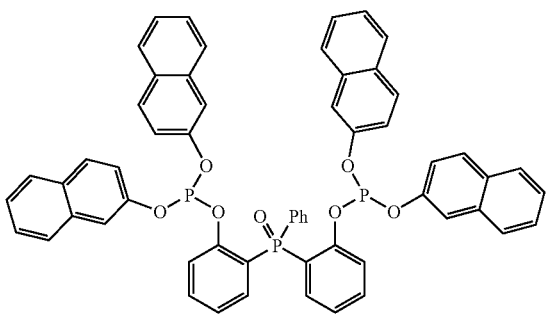
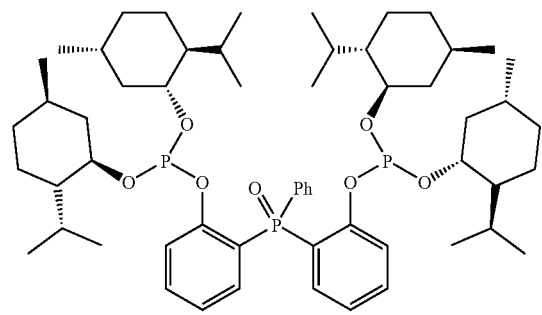
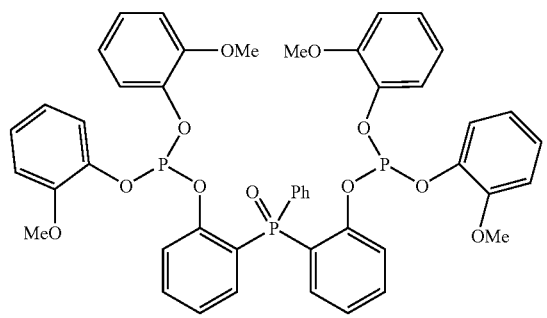
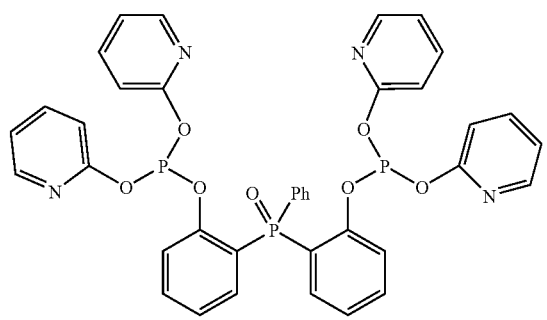
TABLE II-continued
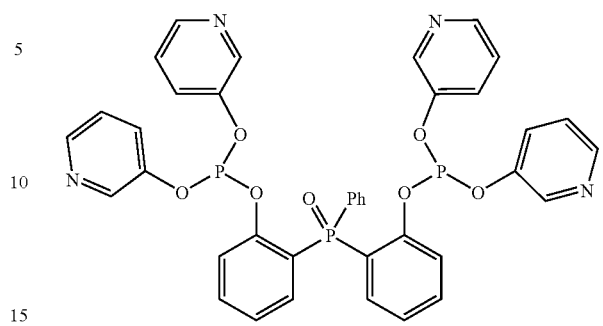
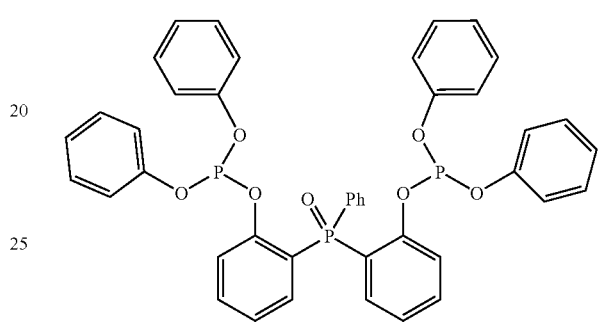
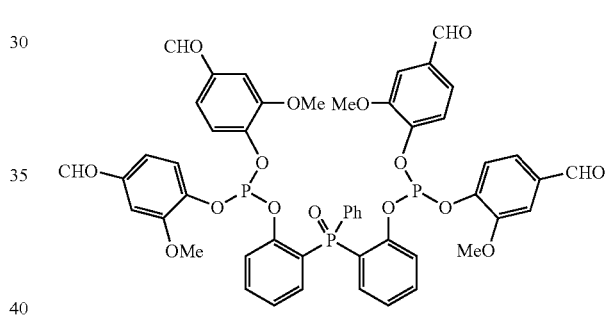
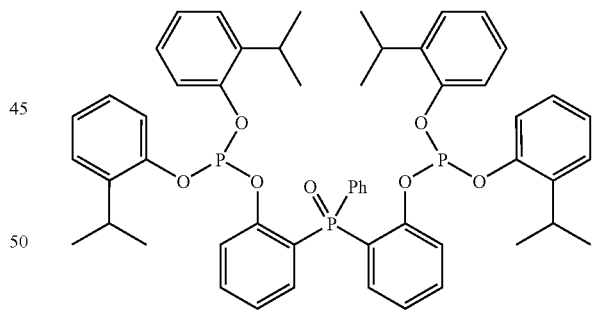
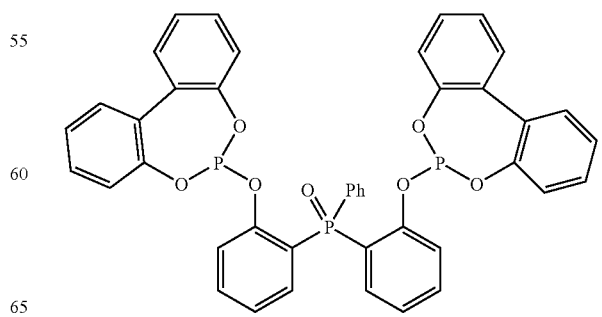

TABLE II-continued

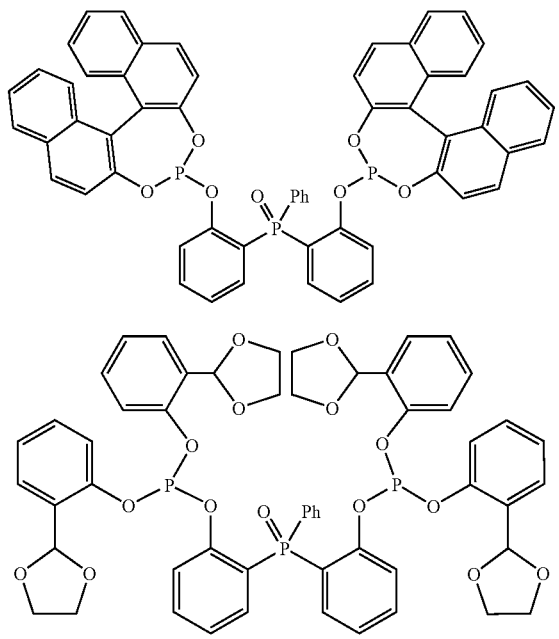

According to the invention the catalyst corresponds advantageously to the general formula (II):

$$M[L_f]_t \quad (II)$$

in which

M is a transition metal, $L_f$ represents the organic ligand of formula (I) and t represents a number between 1 and 4 (inclusive).

Metals which may be complexed by the organic ligands of the invention are generally all transition metals of groups 1b, 2b, 3b, 4b, 5b, 6b, 7b and 8 of the Periodic Table of the Elements, as published in the "Handbook of Chemistry and Physics", 51st Edition (1970-1971) from The Chemical Rubber Company.

Among these metals mention may be made more particularly, as non-limiting examples, of nickel, cobalt, iron, ruthenium, rhodium, palladium, osmium, iridium, platinum, copper, silver, gold, zinc, cadmium and mercury.

Organometallic complexes comprising the organic ligands of the invention may be prepared by contacting a solution of a compound of the selected metal with a solution of the organic ligand of the invention.

The metal compound may be dissolved in a solvent.

The metal in the compound employed may be in the same oxidation state which it will have in the organometallic complex or in a higher oxidation state.

By way of example it is possible to indicate that in the organometallic complexes of the invention rhodium is in oxidation state (I), ruthenium in oxidation state (II), platinum in oxidation state (0), palladium in oxidation state (0), osmium in oxidation state (II), iridium in oxidation state (I), cobalt in oxidation stage (I) and nickel in oxidation state (0).

If in the course of the preparation of the organometallic complex the metal is employed in a higher oxidation state it will be possible for it to be reduced in situ.

The organometallic complexes comprising the organic ligands of the invention may be used as catalysts in olefin hydrocyanation reactions.

As transition metal the transition metal compounds, more particularly the compounds of nickel, of palladium, of cobalt, of iron or of copper, are preferably used.

Among the aforementioned compounds the most preferred compounds are those of nickel.

Non-limiting examples include:

compounds in which nickel is in oxidation state zero, such as potassium tetracyanonickelate $K_4[Ni(CN)_4]$, bis(acrylonitrile)nickel zero, bis(cycloocta-1,5-diene) nickel zero (also called $Ni(cod)_2$) and derivatives containing ligands, such as tetrakis(triphenylphosphine) nickel zero;

compounds of nickel such as carboxylates (especially the acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, aryl- and alkylsulphonates.

When the nickel compound used corresponds to a nickel oxidation state greater than zero a nickel reducing agent which reacts preferentially with the nickel under the reaction conditions is added to the reaction mixture. This reducing agent may be organic or inorganic. Non-limiting examples include borohydrides such as $BH_4Na$ and $BH_4K$, Zn powder, magnesium or hydrogen.

When the nickel compound used corresponds to the zero oxidation state of nickel it is also possible to add a reducing agent of the aforementioned type, but such addition is not mandatory.

When an iron compound is used the same reducing agents are suitable.

In the case of palladium the reducing agents may be, furthermore, elements of the reaction mixture (phosphine, solvent, olefin).

The organic compounds containing at least one ethylenic double bond that are more particularly employed in the present process are diolefins such as butadiene, isoprene, hexa-1,5-diene, cycloocta-1,5-diene, ethylenically unsaturated aliphatic nitriles, especially linear pentenenitriles such as pent-3-enenitrile and pent-4-enenitrile, monoolefins such as styrene, methylstyrene, vinylnaphthalene, cyclohexene, methylcyclohexene and mixtures of two or more of these compounds.

The pentenenitriles in particular may contain amounts, generally minor amounts, of other compounds, such as 2-methylbut-3-enenitrile, 2-methylbut-2-enenitrile, pent-2-enenitrile, valeronitrile, adiponitrile, 2-methylglutaronitrile, 2-ethylsuccinonitrile or butadiene, originating for example from the prior hydrocyanation reaction of the butadiene to unsaturated nitrites.

The reason for this is that the hydrocyanation of the butadiene is accompanied by the formation, along with the linear pentenenitriles, of not inconsiderable amounts of 2-methylbut-3-enenitrile and 2-methylbut-2-enenitrile.

The catalyst system used for the hydrocyanation according to the process of the invention may be prepared before it is introduced into the reaction zone; for example by adding the appropriate amount of selected transition metal compound and where appropriate of reducing agent to the ligand in accordance with the invention, alone or in solution in a solvent. It is also possible to prepare the catalyst system "in situ" by simply adding the ligand and the transition metal compound to the hydrocyanation reaction mixture before or after adding the compound to be hydrocyanated.

The amount of compound of nickel or of another transition metal used is selected so as to give a concentration, in moles of transition metal per mole of organic compounds to be hydrocyanated or isomerized, of between $10^{-4}$ and 1, and preferably between 0.005 and 0.5 mol of nickel or of the other transition metal employed.

The amount of organic ligands of the invention used to form the catalyst is selected such that the number of moles of this compound relative to 1 mol of transition metal is from 0.5 to 50 and preferably from 1 to 10.

Although the reaction is generally conducted without solvent it may be advantageous to add an inert organic solvent. The solvent may be a solvent for the catalyst which is miscible with the phase comprising the compound to be hydrocyanated at the hydrocyanation temperature. Examples of such solvents include aromatic, aliphatic or cycloaliphatic hydrocarbons.

This solvent may also be partially miscible with the compounds to be hydrocyanated, particularly when the reaction mixture is at a temperature lower than the reaction temperature. Hence at such temperatures a two-phase system may be obtained. Where the catalyst system is soluble in said solvent its extraction from the reaction mixture is thereby facilitated. Partially or immiscible solvents of this kind may be water or organic salts in melt form with an ionic character. Such solvents are used particularly when the organic ligand contains anionic radicals which render it soluble in ionic media. These radicals are, for example, sulphonate, carbonate, carboxylate, phosphate, ammonium, guanidinium and imidazolium groups which are substituents on the aromatic radicals of the ligand.

The hydrocyanation reaction is generally carried out at a temperature from 10° C. to 200° C. and preferably from 30° C. to 120° C. Advantageously it is carried out in a single-phase medium at the reaction temperature.

The process of the invention may be implemented continuously or batchwise.

The hydrogen cyanide employed may be prepared from metal cyanides, especially sodium cyanide, or from cyanohydrins, such as acetone cyanohydrin, or by any other known synthesis process.

The hydrogen cyanide is introduced into the reactor in gaseous form, as a gas mixture or in liquid form. It may also be dissolved beforehand in an organic solvent.

In the context of a batchwise implementation it is possible in practice to charge a reactor, purged beforehand by means of an inert gas (such as nitrogen or argon) either with a solution containing the entirety or a part of the various constituents, such as the organic ligand of the invention, the transition metal compound, the reducing agents and solvents where appropriate, or with said constituents separately. Generally the reactor is then taken to the selected temperature and then the compound to be hydrocyanated is introduced. The hydrogen cyanide is then itself introduced, preferably continuously and regularly.

When the reaction (whose development can be monitored by assaying samples) is at an end the reaction mixture is withdrawn, after cooling, and the reaction products are isolated, by distillation for example.

An enhancement of the process for hydrocyanating ethylenically unsaturated compounds according to the present invention relates in particular to the hydrocyanation of said ethylenically unsaturated nitrile compounds by reaction with hydrogen cyanide and consists in using a catalyst system in accordance with the present invention with a cocatalyst composed of at least one Lewis acid.

The ethylenically unsaturated compounds which may be employed in this improvement are in general those which were mentioned for the basic process. However, it is more particularly advantageous to apply it to the hydrocyanation reaction to dinitriles of the ethylenically unsaturated aliphatic mononitriles, particularly to apply it to linear pentenenitriles such as pent-3-enenitrile, pent-4-enenitrile and mixtures thereof.

These pentenenitriles may contain amounts, generally minor amounts, of other compounds, such as 2-methylbut-3-enenitrile, 2-methylbut-2-enenitrile, pent-2-enenitrile, valeronitrile, adiponitrile, 2-methylglutaronitrile, 2-ethylsuccinonitrile or butadiene, originating from the prior hydrocyanation reaction of the butadiene and/or from the isomerization of 2-methylbut-3-enenitrile to pentenenitriles.

The Lewis acid used as cocatalyst makes it possible in particular, in the case where ethylenically unsaturated aliphatic nitriles are hydrocyanated, to improve the linearity of the dinitriles obtained, in other words the percentage of linear dinitriles relative to the entirety of the dinitriles formed, and/or to enhance the activity and service life of the catalyst.

A Lewis acid in the present text, according to the usual definition, refers to compounds which accept electron pairs.

Use may be made in particular of the Lewis acids cited in the work edited by G. A. Olah, "Friedel-Crafts and related Reactions", volume I, pages 191 to 197 (1963).

The Lewis acids which may be employed as cocatalysts in the present process are selected from compounds of the elements of groups Ib, IIb, IIIa, IIIb, IVa, IVb, Va, Vb, VIb, VIIb and VIII of the Periodic Table of the Elements. These compounds are most often salts, especially halides, such as chlorides or bromides, sulphates, sulphonates, haloalkylsulphonates, perhaloalkylsulphonates, especially fluoroalkylsulphonates or perfluoroalkylsulphonates, haloalkylacetates, perhaloalkylacetates, especially fluoroalkylacetates or perfluoroalkylacetates, carboxylates and phosphates.

Non-limiting examples of such Lewis acids include zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, indium trifluoroacetate, zinc trifluoroacetate, the chlorides or bromides of rare earth elements such as lanthanum, cerium, praseodymium, neodymium, samarium, europium, gadolinium, terbium, dysprosium, hafnium, erbium, thallium, ytterbium and lutetium, and cobalt chloride, ferrous chloride and yttrium chloride.

As a Lewis acid it is also possible to use organometallic compounds such as triphenylborane or titanium isopropoxide.

It will be appreciated that mixtures of two or more Lewis acids may be employed.

Among Lewis acids particular preference is given to zinc chloride, zinc bromide, stannous chloride, stannous bromide and triphenylborane and to zinc chloride/stannous chloride mixtures, indium trifluoromethylsulphonate, indium trifluoroacetate and zinc trifluoroacetate.

The Lewis acid cocatalyst employed represents generally from 0.01 to 50 mol per mole of transition metal compound, more particularly of nickel compound, and preferably from 0.5 to 10 mol per mole.

As for the implementation of the basic process of the invention, the catalyst solution used for the hydrocyanation in the presence of Lewis acid may be prepared prior to its introduction into the reaction zone; for example, by adding the ligand of formula (I), the appropriate amount of selected transition metal compound, Lewis acid and, where appropriate, reducing agent to the reaction mixture. It is also possible to prepare the catalyst solution "in situ" by simply mixing these various constituents.

It is also possible, under the conditions of the hydrocyanation process of the present invention, and especially when working in the presence of the above-described catalyst comprising at least one ligand of formula (I) and at least one transition metal compound, to carry out the isomerization of 2-methylbut-3-enenitrile to pentenenitriles, and more generally of branched unsaturated nitrites to linear unsaturated nitrites, in the absence of hydrogen cyanide.

The 2-methylbut-3-enenitrile subjected to the isomerization according to the invention may be employed alone or in a mixture with other compounds.

Thus 2-methylbut-3-enenitrile may be deployed as a mixture with 2-methylbut-2-enenitrile, pent-4-enenitrile, pent-3-enenitrile, pent-2-enenitrile, butadiene, adiponitrile, 2-methylglutaronitrile, 2-ethylsuccinonitrile or valeronitrile.

It is particularly advantageous to treat the reaction mixture originating from the hydrocyanation of butadiene by HCN in the presence of at least one ligand of formula (I) and at least one transition metal compound, more preferably a compound of nickel in oxidation state 0, as defined above.

In the context of this preferred version the catalyst system is already present for the butadiene hydrocyanation reaction and it is therefore sufficient to stop any introduction of hydrogen cyanide in order to allow the isomerization reaction to take place.

It is possible, where appropriate, in this version to effect a gentle purging of the reactor by means of an inert gas, such as nitrogen or argon for example, in order to expel the hydrocyanic acid which might still be present.

The isomerization reaction is generally carried out at a temperature from 10° C. to 200° C. and preferably from 60° C. to 160° C.

In the preferred case of an isomerization immediately following the butadiene hydrocyanation reaction it will be advantageous to operate at the temperature at which the hydrocyanation was conducted.

As for the process of hydrocyanating ethylenically unsaturated compounds, the catalyst system used for the isomerization may be prepared prior to its introduction into the reaction zone; for example, by adding the ligand of formula (I), the appropriate amount of selected transition metal compound and, where appropriate, reducing agent to a solvent. It is also possible to prepare the catalyst system "in situ" by simply adding these various constituents to the reaction mixture. The amount of transition metal compound, and more particularly of nickel compound, that is used, and the amount of ligand of formula (I), are the same as for the hydrocyanation reaction.

Although the isomerization reaction is conducted generally without solvent it may be advantageous to add an inert organic solvent, which may be that of the subsequent extraction. This is the case particularly when such a solvent has been employed in the butadiene hydrocyanation reaction that was used to prepare the mixture which is subjected to the isomerization reaction. Such solvents may be selected from those which were identified above for the hydrocyanation.

The preparation of dinitrile compounds by hydrocyanation of an olefin such as butadiene may be carried out using a catalyst system in accordance with the invention for the above steps of formation of unsaturated mononitriles and the isomerization step; the hydrocyanation reaction of unsaturated mononitriles to dinitriles can be implemented with a catalyst system in accordance with the invention or any other catalyst system already known for this reaction.

Similarly the hydrocyanation reaction of the olefin to unsaturated mononitriles and the isomerization thereof may be carried out with a catalyst system other than that of the invention; the hydrocyanation step of the unsaturated mononitriles to dinitriles is employed with a catalyst system in accordance with the invention.

The invention likewise provides organophosphorus compounds corresponding to the general formula I below:

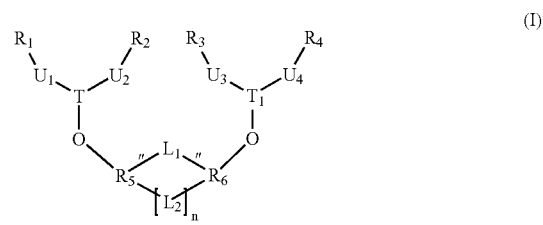

in which:

T and $T_1$, which are identical or different, represent a phosphorus, arsenic or antimony atom, $R_1$, $R_2$, $R_3$ and $R_4$, which are identical or different, represent a substituted or unsubstituted, aromatic, aliphatic or cycloaliphatic radical comprising one or more rings, which are in fused form or not and which may contain one or more heteroatoms, where the radicals $R_1$ and $R_2$ on the one hand and $R_3$ and $R_4$ on the other hand may be interconnected by a covalent bond, a hydrocarbon chain or a heteroatom, $U_1$, $U_2$, $U_3$ and $U_4$, which are identical or different, represent an oxygen atom or a radical of formula NR in which R denotes a monovalent alkyl, aryl, cycloalkyl, sulphonyl or carbonyl radical, $R_5$ and $R_6$, which are identical or different, represent an aryl or cycloaliphatic group which may comprise heteroatoms and/or one or more rings, in fused form or not, and which are substituted or unsubstituted, n is an integer equal to 0 or 1, $L_1$, when n is 0, represents a divalent radical selected from the group consisting of the groups $NR_7$, $PR_8$, $SiR_9R_{10}$, $BR_{11}$, S, $POR_{12}$, $SO_2$ and CO, in which $R_7$ is as defined for R above, $R_8$ and $R_{12}$ may represent the radical $OR_{13}$, and $R_8$, $R_9$, $R_{10}$, $R_{11}$, $R_{12}$ and $R_{13}$ represent alkyl, aryl or cycloalkyl radicals, $L_1$ and $L_2$, when n is 1, are identical or different and represent a covalent bond or a radical selected from the group consisting of the groups O, $NR_7$, $PR_8$, $SiR_9R_{10}$, $BR_{11}$, S, $POR_{12}$, $SO_2$, CO and —$CR_{14}R_{15}$—, in which $R_7$ is as defined for R above, $R_8$ and $R_{12}$ may represent the radical $OR_{13}$, and $R_8$, $R_9$, $R_{10}$, $R_{11}$, $R_{12}$, $R_{13}$, $R_{14}$ and $R_{15}$ represent alkyl, aryl or cycloalkyl radicals, it being possible also for $R_{14}$ and $R_{15}$ to represent a hydrogen atom.

The invention relates in particular to the organophosphorus compounds listed in Table II above.

These compounds are obtained in particular by mixing a solution in toluene of a diphenol compound corresponding to the structure of the following formula:

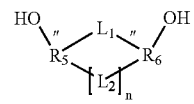

with a toluenic solution of a chlorophosphite of following formula(e):

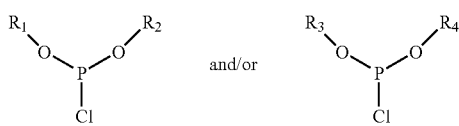

In the above formulae the symbols have the same meanings as in formula I.

The mixture is stirred for a number of hours (of the order of 8 to 15 hours) at ambient temperature (between 15° C. and 30° C.). The organophosphorus compound is recovered, for example, by filtering the mixture.

This preparation procedure is given solely by way of example and indication. Other preparation processes may be used without departing from the scope of the invention.

Moreover, the phenols and chlorophosphites are generally available commercially or may be synthesized by conventional processes described for obtaining these compounds.

The examples which follow illustrate the invention.

In the examples the abbreviations used have the meanings indicated below.

cod: 1,5-cyclooctadiene
eq: equivalent
3PN: 3-pentenenitrile
4PN: 4-pentenenitrile
3+4PN: 3PN+4PN
DC(Y): degree of conversion of the product to be hydrocyanated, Y, corresponding to the ratio of the number of moles of Y converted to the initial number of moles of Y
Linearity (L): ratio of the number of moles of adiponitrile (AdN) formed to the number of moles of dinitriles formed (sum of the moles of AdN, ethylsuccinonitrile (ESN) and methylglutaronitrile (MGN))
GC: gas chromatography
ml: milliliter
mol: mole(s)
mmol: millimole(s).

The various products in accordance with the invention may be prepared by one of the two following procedures:

Procedure I:

A phosphochloridite is used which is prepared from a phenol or biphenol derivative and $PCl_3$ according to a conventional procedure (see, for example, the method described by G. Buisman et al. in Tetrahedron, Asymmetry, vol. 4, (7), pp. 1625-34 (1993)), and a diol available commercially or obtained by carrying out the process disclosed in patent GB2072161. The following general procedure is representative:

In a 100 ml reactor under argon 6 mmol of phosphochloridite are dissolved in 20 ml of anhydrous toluene. The solution is stirred at −10° C. A solution of 3 mmol of diol and 10 mmol of triethylamine in 20 ml of anhydrous toluene is introduced dropwise into the reaction mixture, which is held at −10° C.: a white precipitate forms. The suspension is stirred vigorously at 25° C. for 18 h and then filtered under argon over a bed of basic alumina. After rinsing with toluene, the filtrate is concentrated under reduced pressure to give the desired product, which is used without further purification.

The following ligands were prepared according to the procedure described above:

| Example | Ligand | Structure | Phosphochloridite | Diol |
|---|---|---|---|---|
| 1 | A | 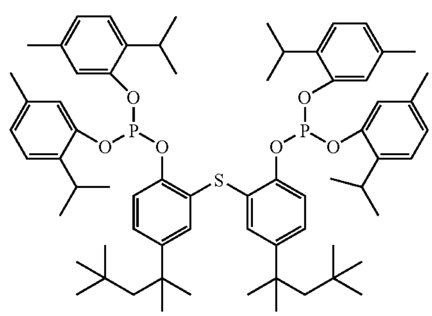 | | |
| 2 | B | 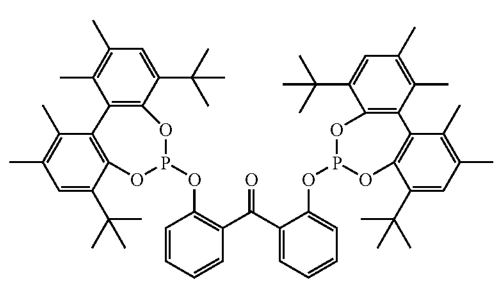 | | |

| Example | Ligand | Structure | Phosphochloridite | Diol |
|---------|--------|-----------|-------------------|------|
| 3 | C | 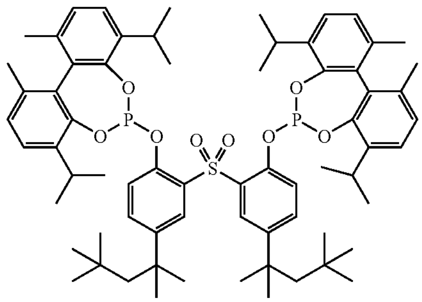 | | |

Procedure II:

A phenol at least substituted un ortho position and a diol available commercially or obtained by carrying out the process disclosed in patent GB2072161A are used according to the following procedure:

In a 100 ml reactor under argon 12 mmol of phenol are dissolved in 20 ml of anhydrous toluene. The solution is stirred at −15° C. 6 mmol of PCl$_3$ are added. 20 mmol of triethylamine are slowly introduced during 1 hour into the reaction mixture, which is held at −15° C.: a white precipitate forms. The suspension is stirred vigorously at −15° C. for 1 h after the end of the addition. A solution of 3 mmol of diol in 20 ml of anhydrous toluene is introduced dropwise into the reaction mixture held at −15° C. : a white precipitate forms. The suspension is stirred vigorously at 25° C. for 18 h and then filtered under argon over a bed of basic alumina. After rinsing with toluene, the filtrate is concentrated under reduced pressure to give the desired product, which is used without further purification.

The following ligands were prepared according to the procedure described above:

| Example | Ligand | Structure | Phenol | Diol |
|---------|--------|-----------|--------|------|
| 4 | D | 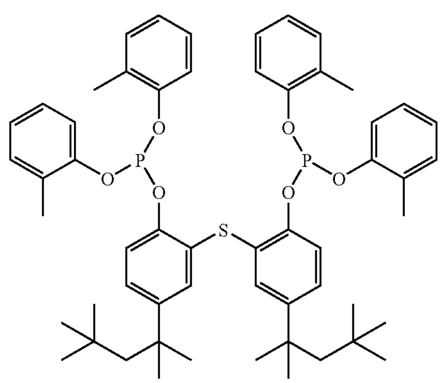 | | |

| Example | Ligand | Structure | Phenol | Diol |
|---|---|---|---|---|
| 5 | E | 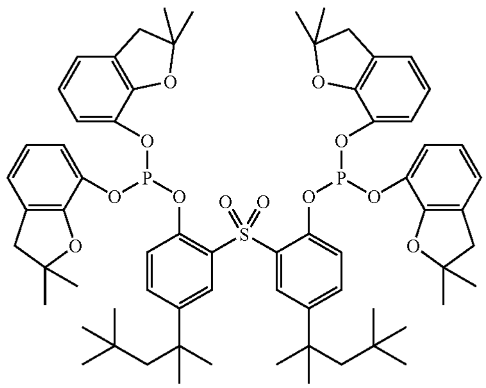 | | |

Procedure III:

A phosphoramidite is used which is prepared from Cl$_2$PNEt$_2$ (available commercially) and a substituted or unsubstituted phenol according to the following procedure:

A mixture of Cl$_2$PNEt$_2$ (0.20 mol) and triethylamine (0.44 mol) in toluene (800 ml) at 0° C. is admixed slowly, with vigorous stirring, with a solution of phenol (0.40 mol) in toluene (100 ml). The formation of a white precipitate is observed. The mixture is allowed to climb to ambient temperature and is stirred, still vigorously, for 2 h. The mixture is subsequently filtered on a bed of silica and concentrated under vacuum to give the phosphoramidite (ArO)$_2$PNEt$_2$ with a purity of more than 95%.

Additionally a commercially available diol or obtained by carrying out the process disclosed in patent GB2072161A is used. The following general procedure is representative:

In a 100 ml reactor under argon 6 mmol of phosphoramidite are introduced in 20 ml of anhydrous toluene. The solution is stirred at 0° C. and 7.5 ml of a 2 M solution of hydrochloric acid in ether are added thereto over 30 minutes. The formation of a white precipitate is observed, and the mixture is stirred at ambient temperature for 1 hour. A solution of 3 mmol of diol and 10 mmol of triethylamine in 20 ml of anhydrous toluene is subsequently introduced dropwise into the reaction mixture, which is cooled at −10° C. The suspension is stirred vigorously at 25° C. for 18 hours and then filtered under argon on a bed of basic alumina. After rinsing with toluene, the filtrate is concentrated under reduced pressure to give the desired product, which is used without further purification.

The following ligands were prepared according to the procedure described above:

| Example | Ligand | Structure | Phenol | Diol |
|---|---|---|---|---|
| 6 | F | 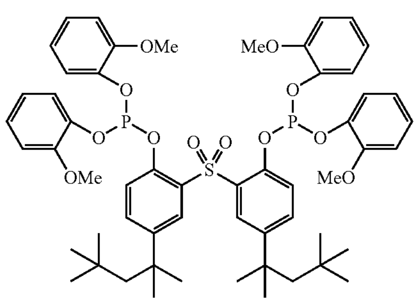 | | |

-continued

| Example | Ligand | Structure | Phenol | Diol |
|---|---|---|---|---|
| 7 | G | 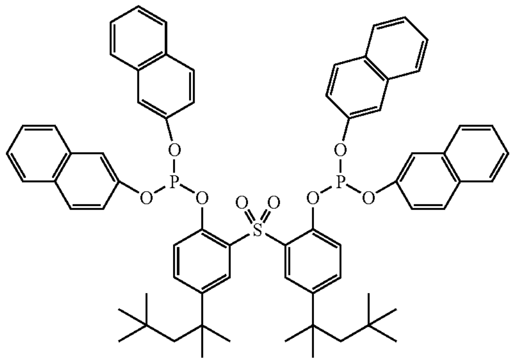 | | |
| 8 | H | 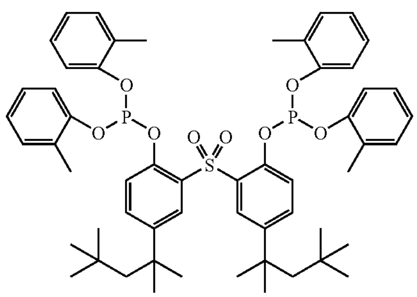 | | |
| 9 | I | 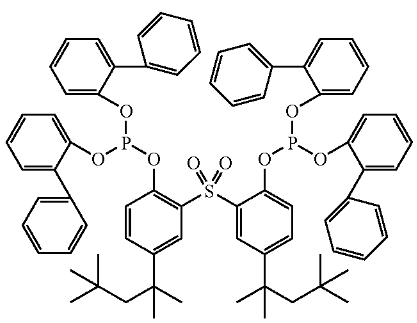 | | |
| 10 | J | 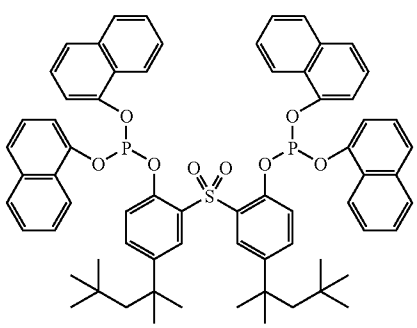 | | |

EXAMPLES OF HYDROCYANATION OF 3-PENTENENITRILE (3PN) TO ADIPONITRILE (AdN)

The general procedure used is as follows:

Under an argon atmosphere a 60 ml Schott glass tube equipped with a septum stopper is charged in succession with the ligand (2.5 eq),
1.21 g (15 mmol; 30 eq) of anhydrous 3PN,
138 mg (0.5 mmol; 1 eq) of Ni(cod)$_2$ and
the Lewis acid (0.5 mmol; 1 eq).

The mixture is taken to 70° C. with stirring. Acetone cyanohydrin is injected into the reaction mixture by means of a syringe driver at a rate of 0.45 ml per hour. After 3 hours of injection the syringe driver is stopped. The mixture is cooled to ambient temperature, diluted with acetone and analysed by gas chromatography.

The results are compiled in the table below:

| Example | Ligand | Lewis acid | DC (3PN) | Linearity |
|---------|--------|------------|----------|-----------|
| 11 | A | In(OCOCF$_3$)$_3$ | 27% | 86% |
| 12 | B | In(OCOCF$_3$)$_3$ | 44% | 78% |
| 13 | C | ZnCl$_2$ | 40% | 73% |
| 14 | D | In(OCOCF$_3$)$_3$ | 44% | 78% |
| 15 | E | ZnCl$_2$ | 23% | 81% |
| 16 | F | ZnCl$_2$ | 65% | 83% |
| 17 | F | In(OCOCF$_3$)$_3$ | 44% | 87% |
| 18 | G | ZnCl$_2$ | 23% | 75% |
| 19 | H | ZnCl$_2$ | 57% | 80% |
| 20 | I | ZnCl$_2$ | 49% | 83% |
| 21 | J | ZnCl$_2$ | 15% | 73% |

The invention claimed is:

1. A process for hydrocyanating an ethylenically unsaturated aliphatic nitrile, or a linear pentenenitrile, by reacting it in a liquid medium with hydrogen cyanide in the presence of a catalyst corresponding to the general formula (II):

$$M[L_f]_t \quad (II)$$

wherein:

M is Ni, $L_f$ represents an organic ligand of formula (I) and t represents a number between 1 and 4 (inclusive) wherein the organic ligand corresponds to the general formula I below:

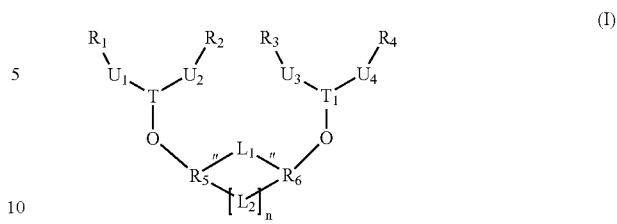

in which:

T and $T_1$, represent a phosphorus atom, $R_1$, $R_2$, $R_3$ and $R_4$ represent a substituted or unsubstituted phenyl group, having one or more rings, which are in fused form or not, optionally having one or more heteroatoms, $U_1$, $U_2$, $U_3$ and $U_4$ represent an oxygen atom, $R_5$ and $R_6$, represent a substituted or unsubstituted phenyl group, n is equal to 0, and $L_1$ represents SO$_2$.

2. The process according to claim 1, wherein the organic ligand of formula I is selected from the group consisting of:

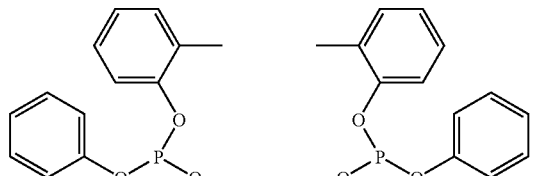

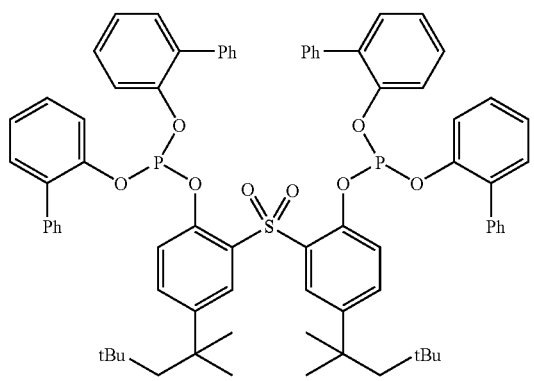

-continued
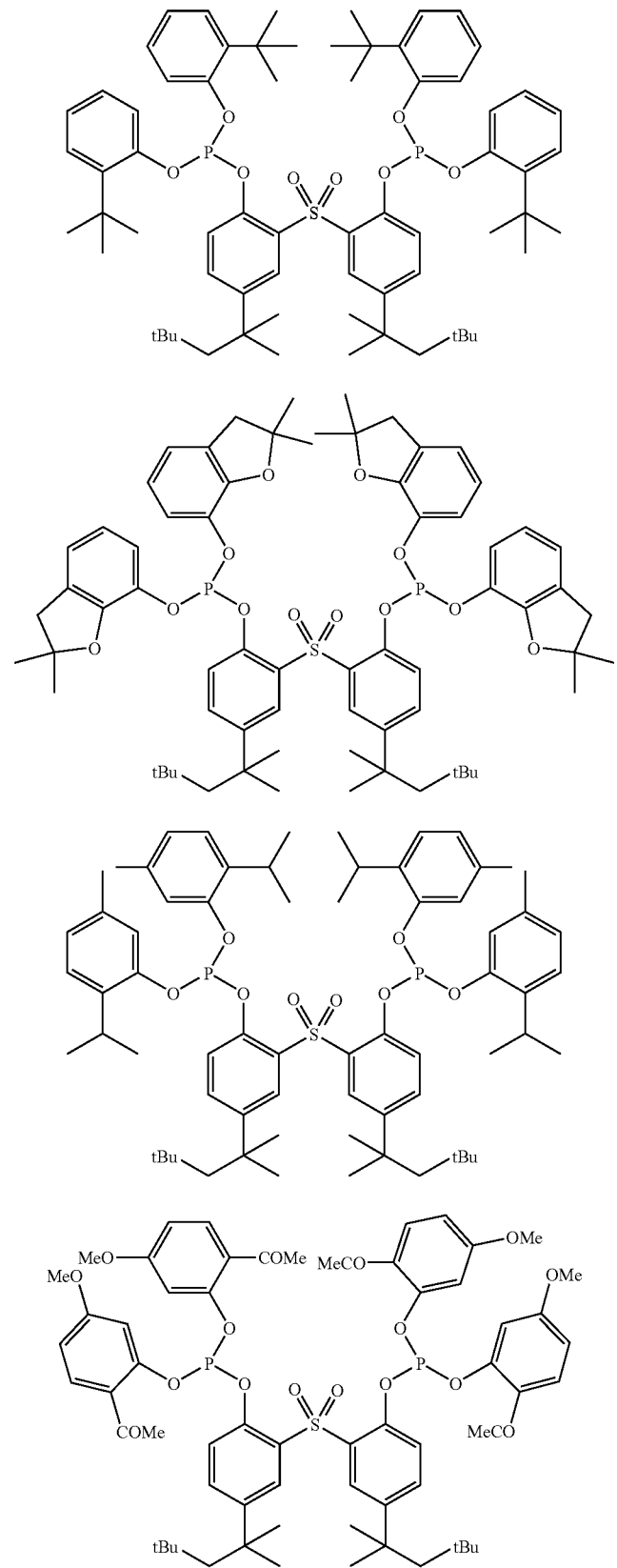

-continued
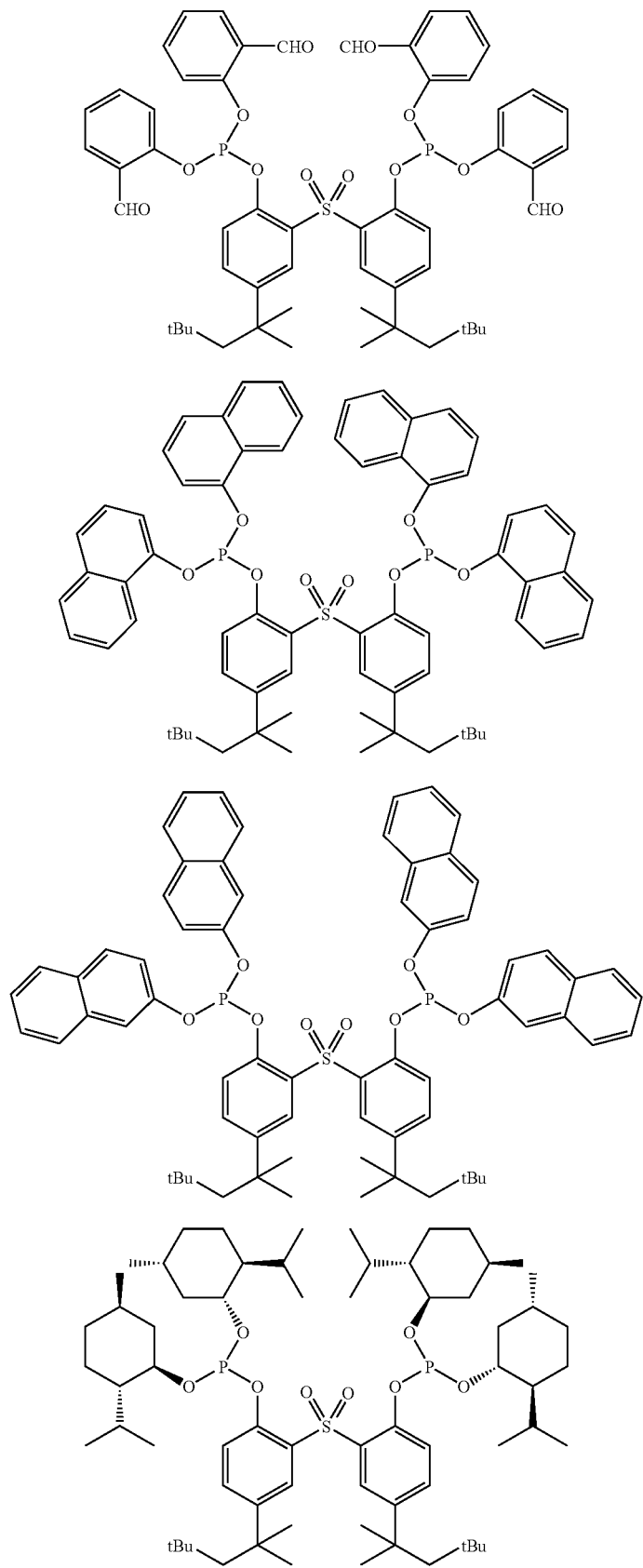

-continued
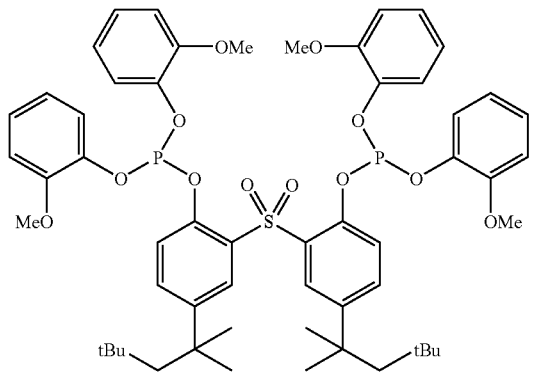
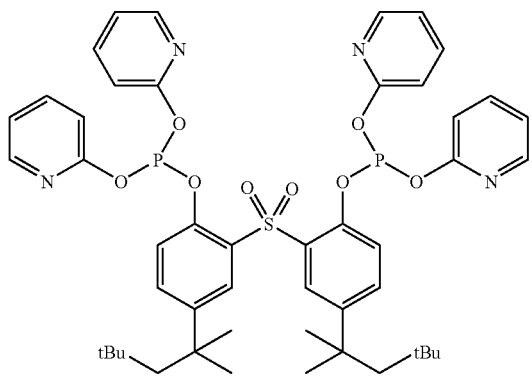
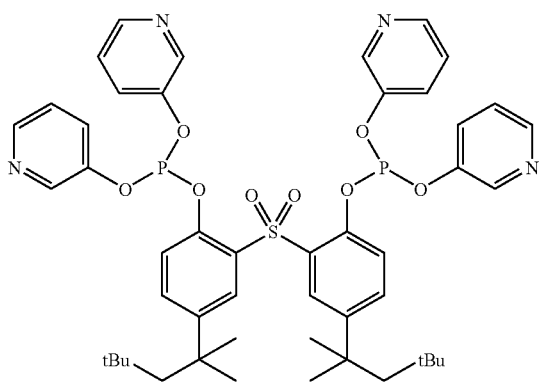
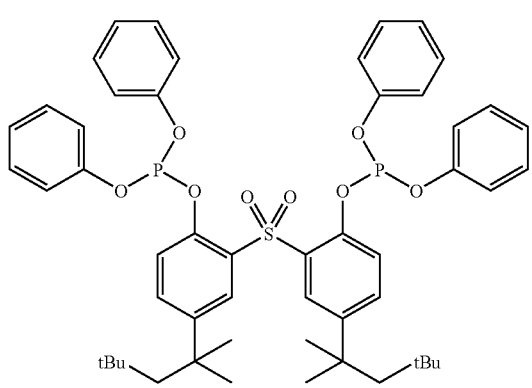

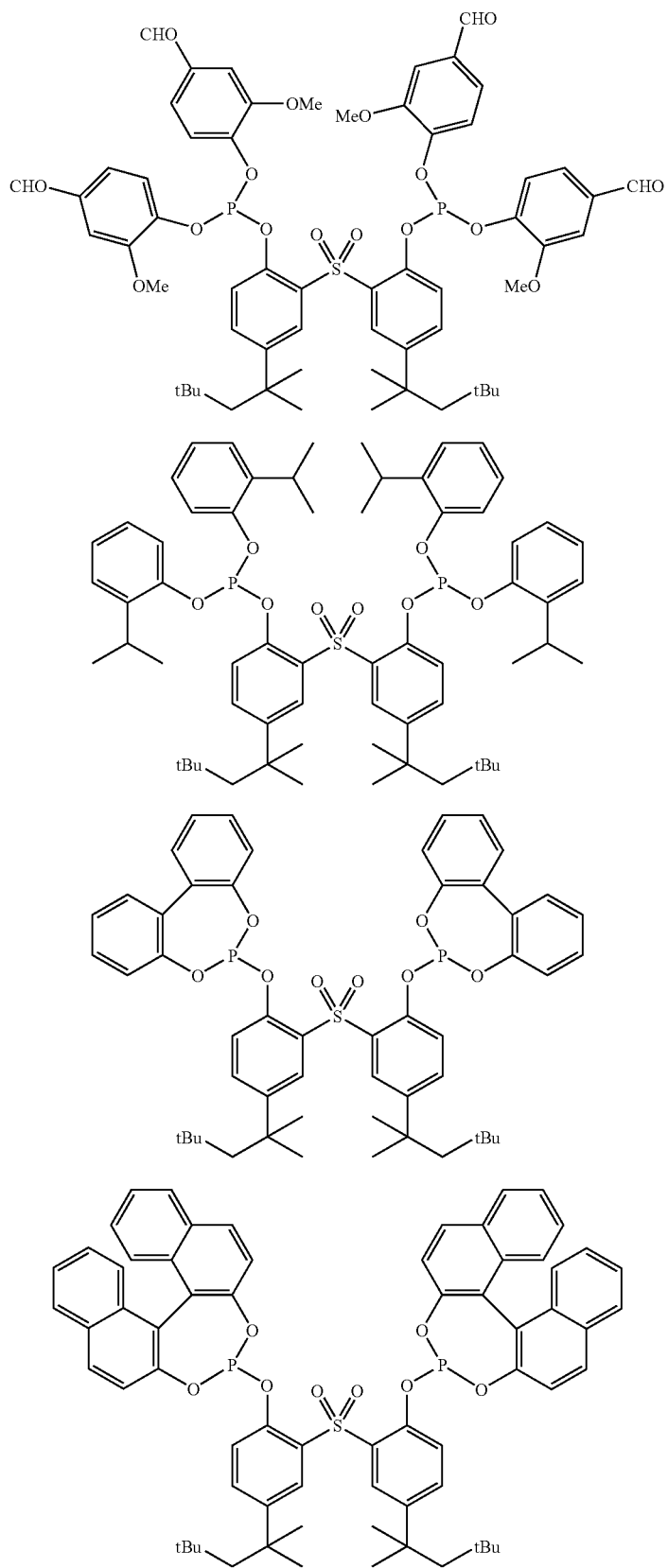

-continued

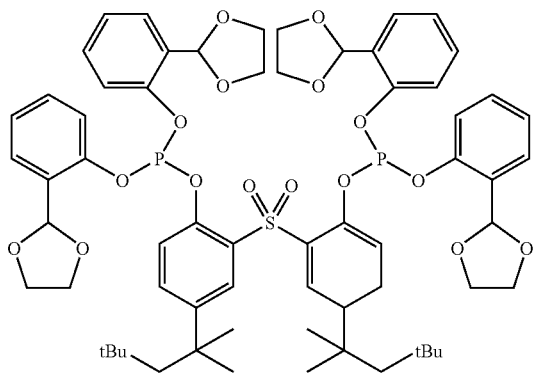

3. The process according to claim 1, wherein the reaction is carried out in a single-phase medium.

4. The process according to claim 1, wherein the liquid medium further comprises a solvent for the catalyst which is miscible with a phase comprising the compound to be hydrocyanated at the hydrocyanation temperature.

5. The process according to claim 1, wherein the transition metal compounds are nickel compounds in which nickel is in oxidation state zero, nickel carboxylates, carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates or alkylsulphonates.

6. The process according to claim 1, wherein the transition metal is used in a amount of between $10^{-4}$ and 1 mol of transition metal per mole of hydrocarbon compound and wherein the organic ligand of formula (I) is used in a number of moles of from 0.5 to 50 relative to 1 mol of transition metal.

7. The process according to claim 1, wherein the hydrocyanation reaction is carried out at a temperature from 10° C. to 200° C.

8. The process according to claim 1 for hydrocyanating ethylenically unsaturated nitrile compounds to dinitriles, being operated in the presence of a catalyst system comprising at least one transition metal compound, at least one organic compound of formula (I) and a cocatalyst composed of at least one Lewis acid.

9. The process according to claim 8, wherein the ethylenically unsaturated nitrile compounds are pent-3-enenitrile, pent-4-enenitrile or mixtures thereof.

10. The process according to claim 9, wherein the linear pentenenitriles contain amounts of other compounds selected from the group consisting of 2-methylbut-3-enenitrile, 2-methylbut-2-enenitrile, pent-2-enenitrile, valeronitrile, adiponitrile, 2-methylglutaronitrile, 2-ethylsuccinonitrile and butadiene.

11. The process according to claim 8, wherein the Lewis acid is selected from salts selected from the group of halides, sulphates, sulphonates, haloalkylsulphonates, perhaloalkylsulphonates, haloalkylacetates, perhaloalkylacetates, carboxylates and phosphates.

12. The process according to claim 8, wherein the Lewis acid is zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, indium trifluoroacetate, zinc trifluoroacetate, lanthanum chloride, cerium chloride, praseodymium chloride, neodymium chloride, samarium chloride, europium chloride, gadolinium chloride, terbium chloride, dysprosium chloride, hafnium chloride, erbium chloride, thallium chloride, ytterbium chloride, lutetium chloride, lanthanum bromide, cerium bromide, praseodymium bromide, neodymium bromide, samarium bromide, europium bromide, gadolinium bromide, terbium bromide, dysprosium bromide, hafnium bromide, erbium bromide, thallium bromide, ytterbium bromide, lutetium bromide, cobalt chloride, ferrous chloride, or yttrium chloride.

13. The process according to claim 8, wherein the Lewis acid employed represents from 0.01 to 50 mol per mole of transition metal compound.

14. The process according to claim 8, wherein 2-methylbut-3-enenitrile, present in the reaction mixture originating from butadiene hydrocyanation, is isomerized to pentenenitriles in the absence of hydrogen cyanide, in the presence of a catalyst comprising at least one organic ligand of general formula (I) and at least one transition metal compound.

15. The process according to claim 14, wherein the 2-methylbut-3-enenitrile subjected to isomerization is employed alone or in a mixture with 2-methylbut-2-enenitrile, pent-4-enenitrile, pent-3-enenitrile, pent-2-enenitrile, butadiene, adiponitrile, 2-methylglutaronitrile, 2-ethylsuccinonitrile or valeronitrile.

16. The process according to claim 14, wherein the isomerization reaction is carried out at a temperature from 10° C. to 200° C.

17. The process according to claim 14, wherein the isomerization of 2-methylbut-3-enenitrile to pentenenitriles is carried out in the presence of at least one transition metal compound, at least one organic phosphorous ligand of the formula (I) and a cocatalyst composed of at least one Lewis acid.

* * * * *